United States Patent
Takano et al.

(10) Patent No.: US 6,551,829 B1
(45) Date of Patent: Apr. 22, 2003

(54) DRYING-RESISTANT, PRACTICAL BAKER'S YEAST

(75) Inventors: Hiroyuki Takano, Ibaraki-ken (JP); Jyun Shima, Ibaraki-ken (JP); Katumi Mori, Ibaraki-ken (JP); Yasuo Suzuki, Chiba-ken (JP); Ryoichi Nakajima, Tokyo (JP); Hajime Watanabe, Saitama-ken (JP)

(73) Assignees: National Food Research Institute, Ministry of Agriculture, Forestry and Fisheries, Ibaraki-Ken (JP); Oriental Yeast Co., Ltd., Tokyo (JP)

( * ) Notice: Subject to any disclaimer, the term of this patent is extended or adjusted under 35 U.S.C. 154(b) by 0 days.

(21) Appl. No.: 09/256,078

(22) Filed: Feb. 24, 1999

(30) Foreign Application Priority Data

Mar. 4, 1998 (JP) .......................................... 10-067672

(51) Int. Cl.⁷ ............................................. C12N 15/64
(52) U.S. Cl. ............. 435/471; 435/254.11; 435/254.21; 426/549
(58) Field of Search ....................... 435/254.11, 254.21, 435/471; 426/549

(56) References Cited

U.S. PATENT DOCUMENTS 5,312,909 A * 5/1994 Driessen et al. ........... 536/23.2
5,578,461 A * 11/1996 Sherwin et al.
5,580,734 A * 12/1996 Treco et al.

OTHER PUBLICATIONS

Klaassen et al., Folia Microbiologica, vol. 39 (1994) pp. 524–526.*
Takano et al., "Effect of Disruption of Neutral Trehalase Gene (NTH1) in Practical Baker's Yeast Strain" The Food Engineering Society of Japan, (Mar. 1997).
Kim et al., "Disruption of the Yeast ATH1 Gene Confers Better Survival after Dehydration, Freezing, and Ethanol Shock: Potential Commercial Application", *Applied and Enviromental Microbiology,* vol. 62, No. 5 pp. 1563–1569.
Gunge et al., "Genetic Mechanisms of Rare Matings of the Yeast *Saccharomyces Cerevisiae* Heterozygous for Mating Type", *Genetics,* vol. 70, pp. 41–58, (1972).
Nakatomi et al., "Saccharomyces Species FD 612 and its use", (1983).
Rose et al., "Structure and function of the yeast URA3 gene: expression in *Escherichia coli*", *Gene.,* vol. 29 pp. 113–124, (1984).
Kopp et al., "Molecular Analysis of the Neutral Trehalase Gene from *Saccharomyces cerevisiae*", *The Journal of Biological Chemistry,* vol. 268, No. 7, pp. 4766–4774, (1993).
Destruelle et al., "Isolation and Characterization of a Novel Yeast Gene, ATH1, that is Required for Vacuolar Acid Trehalase Activity", *Yeast,* vol. 11, pp. 1015–1025, (1995).
Mortimer, "Yeast Genetic Stock Center", (1991).

* cited by examiner

*Primary Examiner*—James Ketter
(74) *Attorney, Agent, or Firm*—Browdy and Neimark

(57) ABSTRACT

Disclosed is a dry baker's yeast of a diploid, practical baker's yeast, which is obtained by mating an ATH1 and/or NTH1 gene-disrupted, haploid yeast as produced through gene manipulation of disrupting the ATH1 and/or NTH1 gene in an a-type haploid yeast of which the diploid is practical baker's yeast, with an ATH1 and/or NTH1 gene-disrupted, haploid yeast as produced through gene manipulation of disrupting the ATH1 and/or NTH1 gene in an α-type haploid yeast of which the diploid is practical baker's yeast. The dry yeast does not require sugared water for its re-activation but can be rapidly re-activated only with water. Using the yeast, therefore, breads having good taste can be produced within a short period of time.

6 Claims, 13 Drawing Sheets

FIG. 1

| | | | | | | | | | | | | | | | |
|---|---|---|---|---|---|---|---|---|---|---|---|---|---|---|---|
| ATG | AGT | CAA | GTT | AAT | ACA | AGC | CAA | GGA | CCG | GTA | GCC | CAA | GGC | CGT | 45 |
| Met | Ser | Gln | Val | Asn | Thr | Ser | Gln | Gly | Pro | Val | Ala | Gln | Gly | Arg | |
| | | | | 5 | | | | | 10 | | | | | 15 | |
| CAA | AGA | AGA | TTA | TCA | TCA | CTA | AGT | GAA | TTC | AAT | GAT | CCA | TTT | TCG | 90 |
| Gln | Arg | Arg | Leu | Ser | Ser | Leu | Ser | Glu | Phe | Asn | Asp | Pro | Phe | Ser | |
| | | | | 20 | | | | | 25 | | | | | 30 | |
| AAC | GCA | GAA | GTC | TAC | TAT | GGC | CCC | CCA | ACA | GAC | CCA | AGA | AAG | CAG | 135 |
| Asn | Ala | Glu | Val | Tyr | Tyr | Gly | Pro | Pro | Thr | Asp | Pro | Arg | Lys | Gln | |
| | | | | 35 | | | | | 40 | | | | | 45 | |
| AAG | CAG | GCA | AAG | CCC | GCT | AAG | ATC | AAC | CGT | ACG | AGG | ACT | ATG | AGT | 180 |
| Lys | Gln | Ala | Lys | Pro | Ala | Lys | Ile | Asn | Arg | Thr | Arg | Thr | Met | Ser | |
| | | | | 50 | | | | | 55 | | | | | 60 | |
| GTT | TTC | GAT | AAT | GTA | TCT | CCT | TTC | AAG | AAA | ACT | GGT | TTT | GGT | AAA | 225 |
| Val | Phe | Asp | Asn | Val | Ser | Pro | Phe | Lys | Lys | Thr | Gly | Phe | Gly | Lys | |
| | | | | 65 | | | | | 70 | | | | | 75 | |
| CTT | CAA | CAG | ACT | AGA | CGT | GGT | TCT | GAG | GAT | GAC | ACC | TAT | TCA | AGT | 270 |
| Leu | Gln | Gln | Thr | Arg | Arg | Gly | Ser | Glu | Asp | Asp | Thr | Tyr | Ser | Ser | |
| | | | | 80 | | | | | 85 | | | | | 90 | |
| AGT | CAA | GGT | AAT | CGT | CGT | TTC | TTT | ATC | GAA | GAT | GTC | GAT | AAA | ACA | 315 |
| Ser | Gln | Gly | Asn | Arg | Arg | Phe | Phe | Ile | Glu | Asp | Val | Asp | Lys | Thr | |
| | | | | 95 | | | | | 100 | | | | | 105 | |
| CTT | AAT | GAA | CTA | CTG | GCT | GCT | GAG | GAT | ACC | GAT | AAA | AAT | TAT | CAG | 360 |
| Leu | Asn | Glu | Leu | Leu | Ala | Ala | Glu | Asp | Thr | Asp | Lys | Asn | Tyr | Gln | |
| | | | | 110 | | | | | 115 | | | | | 120 | |
| ATC | ACC | ATC | GAG | GAT | ACC | GGT | CCA | AAA | GTT | TTG | AAA | GTC | GGT | ACC | 405 |
| Ile | Thr | Ile | Glu | Asp | Thr | Gly | Pro | Lys | Val | Leu | Lys | Val | Gly | Thr | |
| | | | | 125 | | | | | 130 | | | | | 135 | |
| GCA | AAC | TCC | TAT | GGC | TAT | AAG | CAT | ATT | AAT | ATT | AGG | GGT | ACG | TAT | 450 |
| Ala | Asn | Ser | Tyr | Gly | Tyr | Lys | His | Ile | Asn | Ile | Arg | Gly | Thr | Tyr | |
| | | | | 140 | | | | | 145 | | | | | 150 | |
| ATG | TTA | TCC | AAT | TTG | TTG | CAG | GAA | CTA | ACT | ATT | GCG | AAA | AGT | TTT | 495 |
| Met | Leu | Ser | Asn | Leu | Leu | Gln | Glu | Leu | Thr | Ile | Ala | Lys | Ser | Phe | |
| | | | | 155 | | | | | 160 | | | | | 165 | |
| GGT | AGA | CAC | CAA | ATT | TTC | TTA | GAT | GAA | GCT | CGT | ATA | AAC | GAA | AAT | 540 |
| Gly | Arg | His | Gln | Ile | Phe | Leu | Asp | Glu | Ala | Arg | Ile | Asn | Glu | Asn | |
| | | | | 170 | | | | | 175 | | | | | 180 | |
| CCC | GTC | AAC | AGA | TTA | TCA | AGA | TTG | ATA | AAC | ACA | CAG | TTC | TGG | AAC | 585 |
| Pro | Val | Asn | Arg | Leu | Ser | Arg | Leu | Ile | Asn | Thr | Gln | Phe | Trp | Asn | |
| | | | | 185 | | | | | 190 | | | | | 195 | |

FIG. 2

```
TCT TTG ACC AGG AGA GTT GAT CTG AAC AAC GTA GGC GAA ATT GCA    630
Ser Leu Thr Arg Arg Val Asp Leu Asn Asn Val Gly Glu Ile Ala
            200                 205                 210
AAA GAT ACC AAG ATT GAT ACG CCG GGG GCA AAA AAT CCA AGA ATC    675
Lys Asp Thr Lys Ile Asp Thr Pro Gly Ala Lys Asn Pro Arg Ile
            215                 220                 225
TAT GTT CCT TAT GAT TGT CCA GAA CAA TAC GAA TTT TAT GTT CAA    720
Tyr Val Pro Tyr Asp Cys Pro Glu Gln Tyr Glu Phe Tyr Val Gln
            230                 235                 240
GCT TCT CAA ATG CAT CCA TCT TTG AAA TTA GAA GTT GAA TAT TTA    765
Ala Ser Gln Met His Pro Ser Leu Lys Leu Glu Val Glu Tyr Leu
            245                 250                 255
CCA AAA AAA ATA ACG GCA GAA TAC GTC AAA TCC GTC AAT GAT ACC    810
Pro Lys Lys Ile Thr Ala Glu Tyr Val Lys Ser Val Asn Asp Thr
            260                 265                 270
CCC GGT TTA CTA GCA TTG GCT ATG GAA GAG CAC TTC AAT CCT TCT    855
Pro Gly Leu Leu Ala Leu Ala Met Glu Glu His Phe Asn Pro Ser
            275                 280                 285
ACT GGT GAA AAA ACT CTC ATT GGT TAC CCT TAT GCT GTT CCT GGT    900
Thr Gly Glu Lys Thr Leu Ile Gly Tyr Pro Tyr Ala Val Pro Gly
            290                 295                 300
GGT AGA TTC AAT GAA TTA TAT GGT TGG GAC TCC TAT ATG ATG GCA    945
Gly Arg Phe Asn Glu Leu Tyr Gly Trp Asp Ser Tyr Met Met Ala
            305                 310                 315
CTA GGT CTC CTA GAA GCC AAC AAG ACT GAT GTT GCA AGA GGT ATG    990
Leu Gly Leu Leu Glu Ala Asn Lys Thr Asp Val Ala Arg Gly Met
            320                 325                 330
GTG GAG CAT TTT ATT TTT GAG ATT AAT CAC TAT GGA AAA ATA TTG   1035
Val Glu His Phe Ile Phe Glu Ile Asn His Tyr Gly Lys Ile Leu
            335                 340                 345
AAT GCT AAC AGA AGC TAC TAT CTA TGT AGA TCA CAG CCC CCA TTC   1080
Asn Ala Asn Arg Ser Tyr Tyr Leu Cys Arg Ser Gln Pro Pro Phe
            350                 355                 360
TTG ACT GAA ATG GCC TTG GTA GTA TTC AAA AAA CTT GGT GGT AGG   1125
Leu Thr Glu Met Ala Leu Val Val Phe Lys Lys Leu Gly Gly Arg
            365                 370                 375
AGT AAT CCC GAT GCT GTG GAT TTG TTG AAA AGA GCT TTC CAA GCA   1170
Ser Asn Pro Asp Ala Val Asp Leu Leu Lys Arg Ala Phe Gln Ala
            380                 385                 390
```

FIG. 3

| | |
|---|---|
| AGC ATA AAA GAG TAC AAA ACT GTT TGG ACC GCA TCT CCA AGG CTT<br>Ser Ile Lys Glu Tyr Lys Thr Val Trp Thr Ala Ser Pro Arg Leu<br>395 400 405 | 1215 |
| GAT CCC GAA ACA GGC TTA TCC AGG TAC CAT CCT AAC GGT CTC GGT<br>Asp Pro Glu Thr Gly Leu Ser Arg Tyr His Pro Asn Gly Leu Gly<br>410 415 420 | 1260 |
| ATT CCT CCG GAA ACT GAA AGT GAT CAC TTC GAT ACC GTT TTA CTA<br>Ile Pro Pro Glu Thr Glu Ser Asp His Phe Asp Thr Val Leu Leu<br>425 430 435 | 1305 |
| CCA TAT GCA TCG AAA CAC GGC GTT ACC TTA GAC GAA TTT AAG CAA<br>Pro Tyr Ala Ser Lys His Gly Val Thr Leu Asp Glu Phe Lys Gln<br>440 445 450 | 1350 |
| CTT TAT AAC GAT GGT AAG ATA AAG GAG CCT AAA TTG GAT GAG TTT<br>Leu Tyr Asn Asp Gly Lys Ile Lys Glu Pro Lys Leu Asp Glu Phe<br>455 460 465 | 1395 |
| TTT CTT CAT GAC CGT GGC GTT AGA GAA TCT GGA CAC GAC ACT ACA<br>Phe Leu His Asp Arg Gly Val Arg Glu Ser Gly His Asp Thr Thr<br>470 475 480 | 1440 |
| TAT AGG TTT GAG GGC GTA TGT GCC TAC CTG GCC ACT ATT GAC CTG<br>Tyr Arg Phe Glu Gly Val Cys Ala Tyr Leu Ala Thr Ile Asp Leu<br>485 490 495 | 1485 |
| AAT TCT CTT CTT TAC AAA TAC GAG ATT GAT ATT GCG GAC TTC ATA<br>Asn Ser Leu Leu Tyr Lys Tyr Glu Ile Asp Ile Ala Asp Phe Ile<br>500 505 510 | 1530 |
| AAG GAA TTC TGC GAC GAC AAA TAT GAA GAT CCT TTA GAC CAT TCT<br>Lys Glu Phe Cys Asp Asp Lys Tyr Glu Asp Pro Leu Asp His Ser<br>515 520 525 | 1575 |
| ATA ACA ACT TCA GCT ATG TGG AAA GAA ATG GCC AAA ATC AGA CAA<br>Ile Thr Thr Ser Ala Met Trp Lys Glu Met Ala Lys Ile Arg Gln<br>530 535 540 | 1620 |
| GAA AAG ATT ACC AAA TAT ATG TGG GAT GAC GAG TCG GGG TTT TTC<br>Glu Lys Ile Thr Lys Tyr Met Trp Asp Asp Glu Ser Gly Phe Phe<br>545 550 555 | 1665 |
| TTT GAC TAC AAC ACA AAA ATC AAG CAC AGA ACG TCA TAC GAA TCC<br>Phe Asp Tyr Asn Thr Lys Ile Lys His Arg Thr Ser Tyr Glu Ser<br>560 565 570 | 1710 |
| GCA ACT ACA TTC TGG GCA TTA TGG GCT GGA CTT GCC ACG AAG GAG<br>Ala Thr Thr Phe Trp Ala Leu Trp Ala Gly Leu Ala Thr Lys Glu<br>575 580 585 | 1755 |

FIG. 4

```
CAA GCA CAG AAA ATG GTG GAG AAA GCA CTA CCC AAG TTA GAG ATG          1800
Gln Ala Gln Lys Met Val Glu Lys Ala Leu Pro Lys Leu Glu Met
                590                 595                 600
CTT GGA GGT TTA GCT GCA TGT ACG GAG CGT TCT CGA GGC CCA ATT          1845
Leu Gly Gly Leu Ala Ala Cys Thr Glu Arg Ser Arg Gly Pro Ile
                605                 610                 615
TCT ATT TCG AGA CCA ATT AGA CAA TGG GAC TAT CCA TTT GGT TGG          1890
Ser Ile Ser Arg Pro Ile Arg Gln Trp Asp Tyr Pro Phe Gly Trp
                620                 625                 630
GCA CCC CAT CAA ATT CTT GCT TGG GAA GGC CTC CGT TCT TAT GGT          1935
Ala Pro His Gln Ile Leu Ala Trp Glu Gly Leu Arg Ser Tyr Gly
                635                 640                 645
TAT TTA ACT GTA ACG AAT AGG CTA GCT TAT AGA TGG CTT TTC ATG          1980
Tyr Leu Thr Val Thr Asn Arg Leu Ala Tyr Arg Trp Leu Phe Met
                650                 655                 660
ATG ACA AAG GCT TTT GTC GAT TAT AAT GGT ATT GTG GTT GAA AAA          2025
Met Thr Lys Ala Phe Val Asp Tyr Asn Gly Ile Val Val Glu Lys
                665                 670                 675
TAT GAT GTC ACA AGA GGA ACA GAT CCT CAT CGT GTT GAA GCA GAA          2070
Tyr Asp Val Thr Arg Gly Thr Asp Pro His Arg Val Glu Ala Glu
                680                 685                 690
TAC GGT AAT CAA GGT GCT GAC TTT AAA GGG GCA GCT ACT GAA GGT          2115
Tyr Gly Asn Gln Gly Ala Asp Phe Lys Gly Ala Ala Thr Glu Gly
                695                 700                 705
TTT GGA TGG GTC AAT GCC CGT TAC ATT CTT GGT TTG AAG TAT ATG          2160
Phe Gly Trp Val Asn Ala Arg Tyr Ile Leu Gly Leu Lys Tyr Met
                710                 715                 720
AAC AGT TAC GAA AGA AGA GAG ATT GGT GCT TGC ATT CCA CCA ATA          2205
Asn Ser Tyr Glu Arg Arg Glu Ile Gly Ala Cys Ile Pro Pro Ile
                725                 730                 735
TCA TTC TTT AGC AGT TTA AGG CCT CAA GAA AGA AAC CTC TAT GGA          2250
Ser Phe Phe Ser Ser Leu Arg Pro Gln Glu Arg Asn Leu Tyr Gly
                740                 745                 750
CTA TAG                                                              2256
Leu ***>
751
```

Fig.7
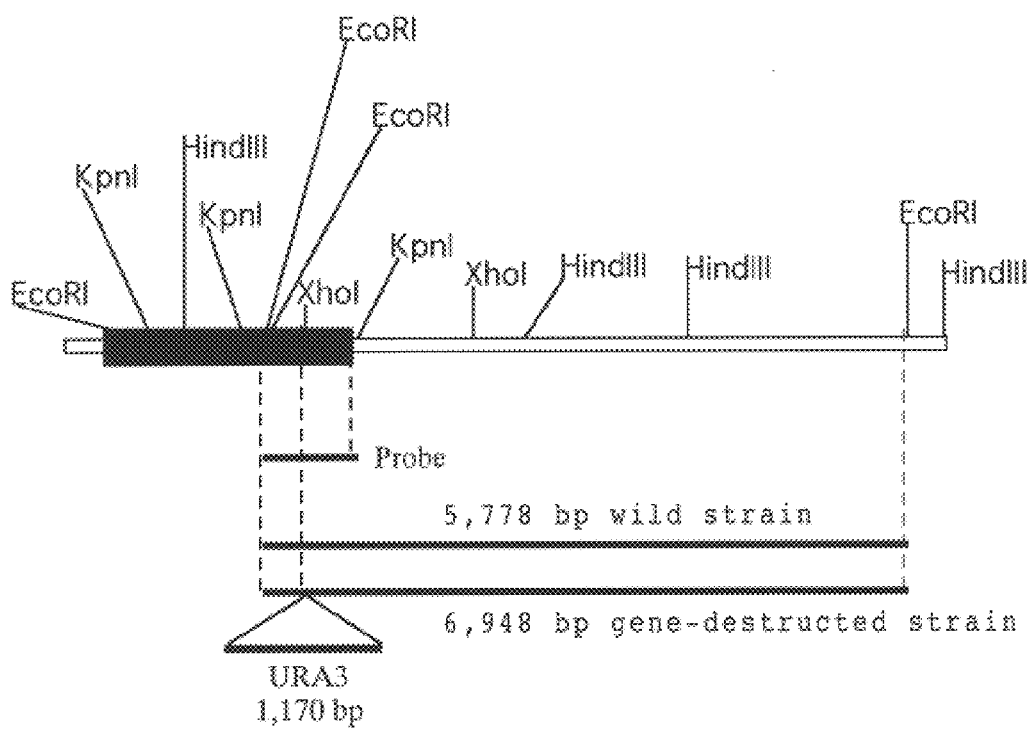
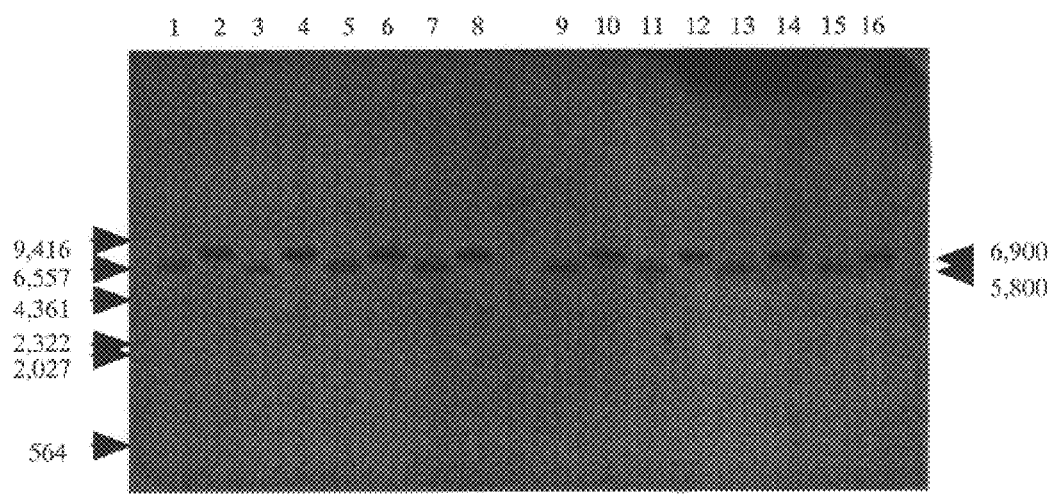

Fig.10
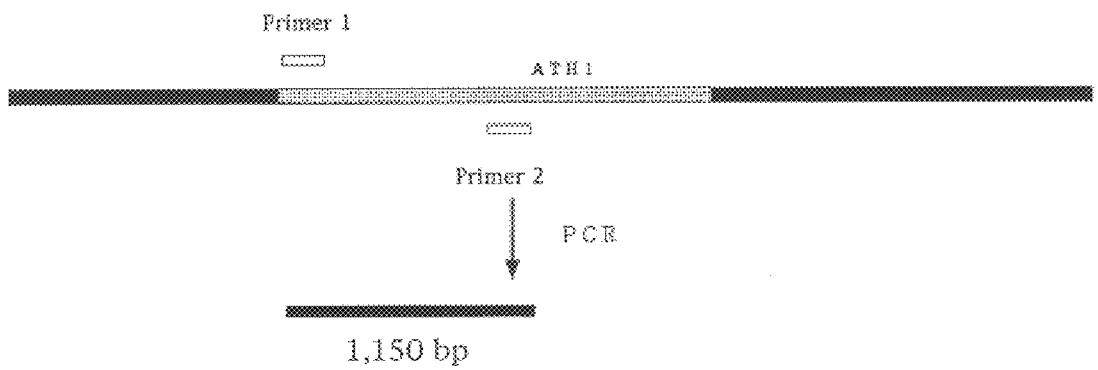
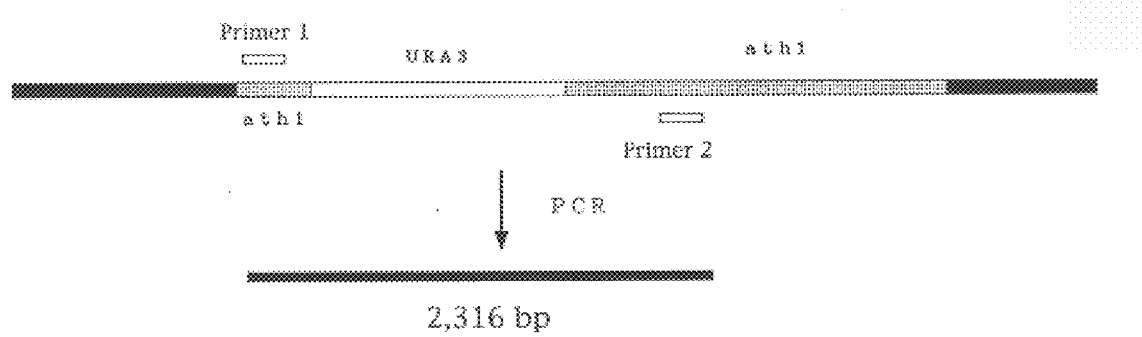
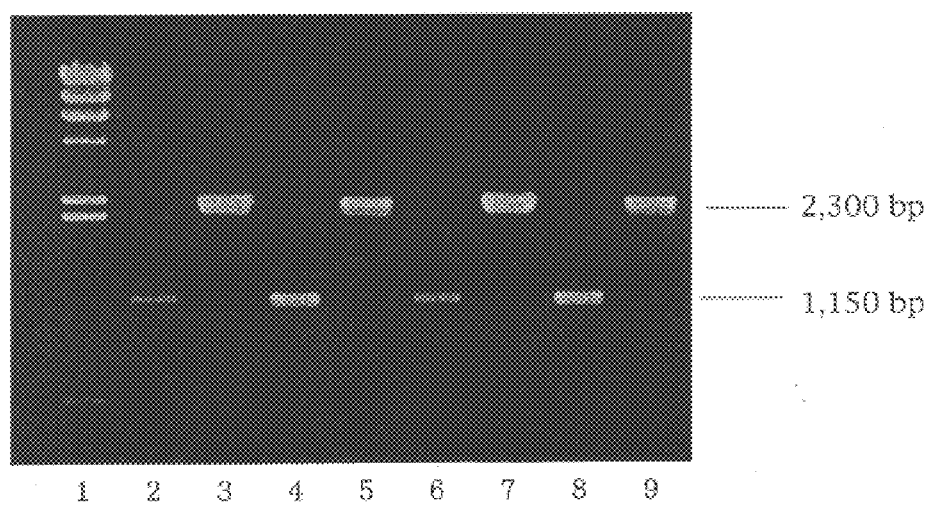

SEQUENCE LISTING

```
<160> NUMBER OF SEQ ID NOS: 6

<210> SEQ ID NO 1
<211> LENGTH: 20
<212> TYPE: DNA
<213> ORGANISM: Saccharomyces cerevisiae

<400> SEQUENCE: 1
catccactgg gagtggtttc                                              20

<210> SEQ ID NO 2
<211> LENGTH: 20
<212> TYPE: DNA
<213> ORGANISM: Saccharomyces cerevisiae

<400> SEQUENCE: 2
cgagatgatt gccaatgtct                                              20

<210> SEQ ID NO 3
<211> LENGTH: 3126
<212> TYPE: DNA
<213> ORGANISM: Saccharomyces cerevisiae
<220> FEATURE:
<221> NAME/KEY: CDS
<222> LOCATION: (1)..(3123)

<400> SEQUENCE: 3 atg att ttg gga agt aac ttg ttc tca aag aat aca tac tcg aga caa      48
Met Ile Leu Gly Ser Asn Leu Phe Ser Lys Asn Thr Tyr Ser Arg Gln
1               5                  10                  15 cca tat gtt gct aac ggt tat ata ggt agt cgt att ccc aat att ggg      96
Pro Tyr Val Ala Asn Gly Tyr Ile Gly Ser Arg Ile Pro Asn Ile Gly
            20                  25                  30 ttc ggc tat gcc tta gac acc ctg aat ttt tac aca gac gca cca ggc     144
Phe Gly Tyr Ala Leu Asp Thr Leu Asn Phe Tyr Thr Asp Ala Pro Gly
        35                  40                  45 gct ttg aat aac ggt tgg ccc tta aga aat cat aga ttt gcc ggt gcg     192
Ala Leu Asn Asn Gly Trp Pro Leu Arg Asn His Arg Phe Ala Gly Ala
    50                  55                  60 ttt gta tcg gac ttt tat tgt cta caa cca aaa cta aat tca aca aac     240
Phe Val Ser Asp Phe Tyr Cys Leu Gln Pro Lys Leu Asn Ser Thr Asn
65                  70                  75                  80 ttc cca gaa ttg gat gat gta gga tat tcc act gtc att tca tct att     288
Phe Pro Glu Leu Asp Asp Val Gly Tyr Ser Thr Val Ile Ser Ser Ile
                85                  90                  95 cca caa tgg acc aat cta cag ttc tca tta gtg aat gat tct aag tgg     336
Pro Gln Trp Thr Asn Leu Gln Phe Ser Leu Val Asn Asp Ser Lys Trp
            100                 105                 110 ttc aat cca caa aat gtt acg ttg gat gac gta act aat tat agc caa     384
Phe Asn Pro Gln Asn Val Thr Leu Asp Asp Val Thr Asn Tyr Ser Gln
        115                 120                 125 aac tta tca atg aag gat ggt atc gta act acg gag tta gat tgg cta     432
Asn Leu Ser Met Lys Asp Gly Ile Val Thr Thr Glu Leu Asp Trp Leu
```

```
                130                    135                    140
aac agt caa ata cat gtt aaa agt gaa atc tgg gca cat cgg cac att        480
Asn Ser Gln Ile His Val Lys Ser Glu Ile Trp Ala His Arg His Ile
145                 150                 155                 160 cat cca ctg gga gtg gtt tct ttg gaa att tcc ctg aat acg gac cat        528
His Pro Leu Gly Val Val Ser Leu Glu Ile Ser Leu Asn Thr Asp His
                165                 170                 175 tta cct tcg gat ttt gat tca tta gat gtt aat ata tgg gat ata ctt        576
Leu Pro Ser Asp Phe Asp Ser Leu Asp Val Asn Ile Trp Asp Ile Leu
            180                 185                 190 gat ttc aac aca tca cat agg act gtt cta cat agc acg gga aca gac        624
Asp Phe Asn Thr Ser His Arg Thr Val Leu His Ser Thr Gly Thr Asp
        195                 200                 205 gaa aaa aat aat gcg gtt ttc atg att gtt cag cca gat aac gtt cca        672
Glu Lys Asn Asn Ala Val Phe Met Ile Val Gln Pro Asp Asn Val Pro
210                 215                 220 tct tct att tgc gct att tac tca acg tgt act gta aag tat gaa aat        720
Ser Ser Ile Cys Ala Ile Tyr Ser Thr Cys Thr Val Lys Tyr Glu Asn
225                 230                 235                 240 tcc acc aat cca ata aat tct agt gaa tct ttt gaa gaa aaa gat gtt        768
Ser Thr Asn Pro Ile Asn Ser Ser Glu Ser Phe Glu Glu Lys Asp Val
                245                 250                 255 tct tct aat att tat aat gtt att ttg aca gag gac caa ccc aag ata        816
Ser Ser Asn Ile Tyr Asn Val Ile Leu Thr Glu Asp Gln Pro Lys Ile
            260                 265                 270 atc gtt cat aag tat gtt ggt att atg tct act gag ttc aat aag aac        864
Ile Val His Lys Tyr Val Gly Ile Met Ser Thr Glu Phe Asn Lys Asn
        275                 280                 285 aaa gaa caa caa gac aat act aat att ggt ttg gcc aaa atg ata gct        912
Lys Glu Gln Gln Asp Asn Thr Asn Ile Gly Leu Ala Lys Met Ile Ala
290                 295                 300 cta aac agt aaa ggc aat tac gag aag ctt ctg tca agt cac aaa cgt        960
Leu Asn Ser Lys Gly Asn Tyr Glu Lys Leu Leu Ser Ser His Lys Arg
305                 310                 315                 320 gcg tgg tat gac ctt tac aac gac gcc ttc att gaa att cct tct gac       1008
Ala Trp Tyr Asp Leu Tyr Asn Asp Ala Phe Ile Glu Ile Pro Ser Asp
                325                 330                 335 agt ctt tta gaa atg aca gca aga tcg tcc cta ttc cat tta cta gca       1056
Ser Leu Leu Glu Met Thr Ala Arg Ser Ser Leu Phe His Leu Leu Ala
            340                 345                 350 aat aca aga gat tac aat gtc tcg agc gat agg ggt ctt ccc gtg gga       1104
Asn Thr Arg Asp Tyr Asn Val Ser Ser Asp Arg Gly Leu Pro Val Gly
        355                 360                 365 gtt tct ggt ttg tca tca gat tcc tat ggt ggt atg gtg ttc tgg gac       1152
Val Ser Gly Leu Ser Ser Asp Ser Tyr Gly Gly Met Val Phe Trp Asp
370                 375                 380 gca gat ata tgg atg gaa cct gcc cta ttg cct ttc ttc cca aat gtg       1200
Ala Asp Ile Trp Met Glu Pro Ala Leu Leu Pro Phe Phe Pro Asn Val
385                 390                 395                 400 gct caa aat atg aat aat tac aga aat gct aca cat tcg cag gca aag       1248
Ala Gln Asn Met Asn Asn Tyr Arg Asn Ala Thr His Ser Gln Ala Lys
                405                 410                 415 tta aat gca gag aaa tat gga tac ccc gga gca ata tac ccc tgg aca       1296
Leu Asn Ala Glu Lys Tyr Gly Tyr Pro Gly Ala Ile Tyr Pro Trp Thr
            420                 425                 430 tct ggt aag tac gct aat tgt act tct acg gga cct tgt gtc gat tac       1344
Ser Gly Lys Tyr Ala Asn Cys Thr Ser Thr Gly Pro Cys Val Asp Tyr
        435                 440                 445 gaa tac cat att aac gtt gat gtc gct atg gcc tcc ttt tcc ata tac       1392
```

-continued

| | | | | | | | | | | | | | | | |
|---|---|---|---|---|---|---|---|---|---|---|---|---|---|---|---|
| Glu | Tyr | His | Ile | Asn | Val | Asp | Val | Ala | Met | Ala | Ser | Phe | Ser | Ile | Tyr |
| | | | 450 | | | | 455 | | | | 460 | | | | |

```
ttg aat gga cac gaa ggg att gat gac gag tat ctg aga tat act aca      1440
Leu Asn Gly His Glu Gly Ile Asp Asp Glu Tyr Leu Arg Tyr Thr Thr
465             470                 475                 480 tgg cca att atc aaa aac gca gcc caa ttt ttt act gct tat gtt aag      1488
Trp Pro Ile Ile Lys Asn Ala Ala Gln Phe Phe Thr Ala Tyr Val Lys
                485                 490                 495 tac aat tct tcc cta gga tta tat gaa aca tat aat ttg aca gat ccc      1536
Tyr Asn Ser Ser Leu Gly Leu Tyr Glu Thr Tyr Asn Leu Thr Asp Pro
                    500                 505                 510 gac gag ttt gct aat cac atc aat aac ggg gct ttc acg aat gct ggc      1584
Asp Glu Phe Ala Asn His Ile Asn Asn Gly Ala Phe Thr Asn Ala Gly
            515                 520                 525 att aaa aca ctt cta aag tgg gca aca gac att ggc aat cat ctc ggc      1632
Ile Lys Thr Leu Leu Lys Trp Ala Thr Asp Ile Gly Asn His Leu Gly
530             535                 540 gag gtc gtt gac ccc aaa tgg agt gaa att tcc aaa gat att tat atc      1680
Glu Val Val Asp Pro Lys Trp Ser Glu Ile Ser Lys Asp Ile Tyr Ile
545             550                 555                 560 cct aga tcc tca tct aac atc act ttg gaa tat tct ggt atg aat agc      1728
Pro Arg Ser Ser Ser Asn Ile Thr Leu Glu Tyr Ser Gly Met Asn Ser
                565                 570                 575 tca gtg gag att aaa cag gcg gat gtg act tta atg gtt tac cca ctt      1776
Ser Val Glu Ile Lys Gln Ala Asp Val Thr Leu Met Val Tyr Pro Leu
                    580                 585                 590 gga tat atc aat gat gaa tcc ata ttg aac aat gca att aaa gat ctt      1824
Gly Tyr Ile Asn Asp Glu Ser Ile Leu Asn Asn Ala Ile Lys Asp Leu
            595                 600                 605 tat tat tat tca gaa aga cag tct gcg tct ggg cct gca atg aca tat      1872
Tyr Tyr Tyr Ser Glu Arg Gln Ser Ala Ser Gly Pro Ala Met Thr Tyr
610             615                 620 ccg gtt ttt gtg gcc gca gct gct ggt ctg ctg aat cac ggc tct tct      1920
Pro Val Phe Val Ala Ala Ala Ala Gly Leu Leu Asn His Gly Ser Ser
625             630                 635                 640 tct caa agt tac tta tat aaa tcg gtt ctt cca tac tta cgg gct cct      1968
Ser Gln Ser Tyr Leu Tyr Lys Ser Val Leu Pro Tyr Leu Arg Ala Pro
                645                 650                 655 ttc gct caa ttt agt gag caa tca gac gac aac ttt tta aca aac gga      2016
Phe Ala Gln Phe Ser Glu Gln Ser Asp Asp Asn Phe Leu Thr Asn Gly
                660                 665                 670 tta acc cag cca gca ttc ccc ttt tta aca gct aac ggt gga ttt cta      2064
Leu Thr Gln Pro Ala Phe Pro Phe Leu Thr Ala Asn Gly Gly Phe Leu
            675                 680                 685 cag agc att ctg ttt ggg tta aca gga atc cga tat tct tat gag gtt      2112
Gln Ser Ile Leu Phe Gly Leu Thr Gly Ile Arg Tyr Ser Tyr Glu Val
690             695                 700 gat cca gat act aaa aaa att aac cgt ttg tta agg ttc aat cca ata      2160
Asp Pro Asp Thr Lys Lys Ile Asn Arg Leu Leu Arg Phe Asn Pro Ile
705             710                 715                 720 gaa cta ccg ttg ctc cct ggt ggt atc gct att aga aac ttc aaa tat      2208
Glu Leu Pro Leu Leu Pro Gly Gly Ile Ala Ile Arg Asn Phe Lys Tyr
                725                 730                 735 atg aac caa gtt tta gat ata ata att gac gac cac aat ggt acg att      2256
Met Asn Gln Val Leu Asp Ile Ile Ile Asp Asp His Asn Gly Thr Ile
                    740                 745                 750 gtt cat aaa tca gga gat gtt cct att cat ata aag ata cca aac aga      2304
Val His Lys Ser Gly Asp Val Pro Ile His Ile Lys Ile Pro Asn Arg
            755                 760                 765
```

-continued

| | | |
|---|---|---|
| tct cta ata cat gac cag gat atc aac ttc tat aat ggt tcc gaa aac<br>Ser Leu Ile His Asp Gln Asp Ile Asn Phe Tyr Asn Gly Ser Glu Asn<br>770                       775                780 | 2352 |
| gaa aga aaa cca aat cta gag cgt aga gac gtc gac cgt gtt ggt gat<br>Glu Arg Lys Pro Asn Leu Glu Arg Arg Asp Val Asp Arg Val Gly Asp<br>785                   790               795                 800 | 2400 |
| cca atg agg atg gat agg tat ggt acc tat tat ctt tta aaa ccg aaa<br>Pro Met Arg Met Asp Arg Tyr Gly Thr Tyr Tyr Leu Leu Lys Pro Lys<br>                805                    810                815 | 2448 |
| caa gag ctt aca gtc caa ctg ttc aag cct ggc tta aac gca aga aac<br>Gln Glu Leu Thr Val Gln Leu Phe Lys Pro Gly Leu Asn Ala Arg Asn<br>820                       825                830 | 2496 |
| aac ata gcg gaa aat aag caa ata aca aac ttg acg gcc ggc gtt cct<br>Asn Ile Ala Glu Asn Lys Gln Ile Thr Asn Leu Thr Ala Gly Val Pro<br>                835                    840                845 | 2544 |
| ggt gac gtt gca ttc tct gct cta gat ggg aat aat tac acg cat tgg<br>Gly Asp Val Ala Phe Ser Ala Leu Asp Gly Asn Asn Tyr Thr His Trp<br>850                       855                860 | 2592 |
| caa ccc tta gac aaa att cac cgt gcg aag cta ttg att gat tta ggt<br>Gln Pro Leu Asp Lys Ile His Arg Ala Lys Leu Leu Ile Asp Leu Gly<br>865                     870               875                 880 | 2640 |
| gaa tac aac gag aaa gag att acc aag gga atg att ctt tgg ggg cag<br>Glu Tyr Asn Glu Lys Glu Ile Thr Lys Gly Met Ile Leu Trp Gly Gln<br>                885                    890                895 | 2688 |
| agg ccc gca aaa aac att tcc ata tct att ttg cct cat tct gaa aaa<br>Arg Pro Ala Lys Asn Ile Ser Ile Ser Ile Leu Pro His Ser Glu Lys<br>900                       905                910 | 2736 |
| gtc gaa aat tta ttt gcg aac gtg aca gaa att atg caa aat tcg gga<br>Val Glu Asn Leu Phe Ala Asn Val Thr Glu Ile Met Gln Asn Ser Gly<br>                915                    920                925 | 2784 |
| aat gat caa ctt ctt aat gaa acc att ggt cag ctt tta gat aat gcc<br>Asn Asp Gln Leu Leu Asn Glu Thr Ile Gly Gln Leu Leu Asp Asn Ala<br>930                       935                940 | 2832 |
| gga att cct gtc gag aac gtt att gat ttt gat ggc ata gaa caa gag<br>Gly Ile Pro Val Glu Asn Val Ile Asp Phe Asp Gly Ile Glu Gln Glu<br>945                     950               955                 960 | 2880 |
| gat gat gaa tct ttg gat gat gtg caa gcc tta ttg cac tgg aag aag<br>Asp Asp Glu Ser Leu Asp Asp Val Gln Ala Leu Leu His Trp Lys Lys<br>                965                    970                975 | 2928 |
| gaa gac tta gcc aag cta att gaa caa ata ccc aga ctt aac ttt cta<br>Glu Asp Leu Ala Lys Leu Ile Glu Gln Ile Pro Arg Leu Asn Phe Leu<br>980                       985                    990 | 2976 |
| aaa aga aaa ttt gtg aaa att ctg gat aac gtg cca gtg agc cca agt<br>Lys Arg Lys Phe Val Lys Ile Leu Asp Asn Val Pro Val Ser Pro Ser<br>                995                   1000              1005 | 3024 |
| gag cca tac tac gaa gca agt cgc aac cag tcg tta atc gag ata<br>Glu Pro Tyr Tyr Glu Ala Ser Arg Asn Gln Ser Leu Ile Glu Ile<br>1010                     1015                   1020 | 3069 |
| tta ccc agt aat aga acg act ttc act att gat tat gat aaa ttt<br>Leu Pro Ser Asn Arg Thr Thr Phe Thr Ile Asp Tyr Asp Lys Phe<br>                1025                   1030                   1035 | 3114 |
| gca ggt ggg tga<br>Ala Gly Gly<br>      1040 | 3126 |

<210> SEQ ID NO 4
<211> LENGTH: 1041
<212> TYPE: PRT
<213> ORGANISM: Saccharomyces cerevisiae

<400> SEQUENCE: 4

```
Met Ile Leu Gly Ser Asn Leu Phe Ser Lys Asn Thr Tyr Ser Arg Gln
1               5                   10                  15

Pro Tyr Val Ala Asn Gly Tyr Ile Gly Ser Arg Ile Pro Asn Ile Gly
            20                  25                  30

Phe Gly Tyr Ala Leu Asp Thr Leu Asn Phe Tyr Thr Asp Ala Pro Gly
            35                  40                  45

Ala Leu Asn Asn Gly Trp Pro Leu Arg Asn His Arg Phe Ala Gly Ala
        50                  55                  60

Phe Val Ser Asp Phe Tyr Cys Leu Gln Pro Lys Leu Asn Ser Thr Asn
65                  70                  75                  80

Phe Pro Glu Leu Asp Asp Val Gly Tyr Ser Thr Val Ile Ser Ser Ile
                85                  90                  95

Pro Gln Trp Thr Asn Leu Gln Phe Ser Leu Val Asn Asp Ser Lys Trp
                100                 105                 110

Phe Asn Pro Gln Asn Val Thr Leu Asp Asp Val Thr Asn Tyr Ser Gln
                115                 120                 125

Asn Leu Ser Met Lys Asp Gly Ile Val Thr Thr Glu Leu Asp Trp Leu
            130                 135                 140

Asn Ser Gln Ile His Val Lys Ser Glu Ile Trp Ala His Arg His Ile
145                 150                 155                 160

His Pro Leu Gly Val Val Ser Leu Glu Ile Ser Leu Asn Thr Asp His
                165                 170                 175

Leu Pro Ser Asp Phe Asp Ser Leu Asp Val Asn Ile Trp Asp Ile Leu
                180                 185                 190

Asp Phe Asn Thr Ser His Arg Thr Val Leu His Ser Thr Gly Thr Asp
            195                 200                 205

Glu Lys Asn Asn Ala Val Phe Met Ile Val Gln Pro Asp Asn Val Pro
210                 215                 220

Ser Ser Ile Cys Ala Ile Tyr Ser Thr Cys Thr Val Lys Tyr Glu Asn
225                 230                 235                 240

Ser Thr Asn Pro Ile Asn Ser Ser Glu Ser Phe Glu Glu Lys Asp Val
                245                 250                 255

Ser Ser Asn Ile Tyr Asn Val Ile Leu Thr Glu Asp Gln Pro Lys Ile
            260                 265                 270

Ile Val His Lys Tyr Val Gly Ile Met Ser Thr Glu Phe Asn Lys Asn
        275                 280                 285

Lys Glu Gln Gln Asp Asn Thr Asn Ile Gly Leu Ala Lys Met Ile Ala
    290                 295                 300

Leu Asn Ser Lys Gly Asn Tyr Glu Lys Leu Leu Ser His Lys Arg
305                 310                 315                 320

Ala Trp Tyr Asp Leu Tyr Asn Asp Ala Phe Ile Glu Ile Pro Ser Asp
            325                 330                 335

Ser Leu Leu Glu Met Thr Ala Arg Ser Ser Leu Phe His Leu Leu Ala
            340                 345                 350

Asn Thr Arg Asp Tyr Asn Val Ser Ser Asp Arg Gly Leu Pro Val Gly
            355                 360                 365

Val Ser Gly Leu Ser Ser Asp Ser Tyr Gly Gly Met Val Phe Trp Asp
    370                 375                 380

Ala Asp Ile Trp Met Glu Pro Ala Leu Leu Pro Phe Phe Pro Asn Val
385                 390                 395                 400

Ala Gln Asn Met Asn Asn Tyr Arg Asn Ala Thr His Ser Gln Ala Lys
                405                 410                 415
```

-continued

```
Leu Asn Ala Glu Lys Tyr Gly Tyr Pro Gly Ala Ile Tyr Pro Trp Thr
            420                 425                 430

Ser Gly Lys Tyr Ala Asn Cys Thr Ser Thr Gly Pro Cys Val Asp Tyr
            435                 440                 445

Glu Tyr His Ile Asn Val Asp Val Ala Met Ala Ser Phe Ser Ile Tyr
            450                 455                 460

Leu Asn Gly His Glu Gly Ile Asp Asp Glu Tyr Leu Arg Tyr Thr Thr
465                 470                 475                 480

Trp Pro Ile Ile Lys Asn Ala Ala Gln Phe Phe Thr Ala Tyr Val Lys
            485                 490                 495

Tyr Asn Ser Ser Leu Gly Leu Tyr Glu Thr Tyr Asn Leu Thr Asp Pro
            500                 505                 510

Asp Glu Phe Ala Asn His Ile Asn Asn Gly Ala Phe Thr Asn Ala Gly
            515                 520                 525

Ile Lys Thr Leu Leu Lys Trp Ala Thr Asp Ile Gly Asn His Leu Gly
            530                 535                 540

Glu Val Val Asp Pro Lys Trp Ser Glu Ile Ser Lys Asp Ile Tyr Ile
545                 550                 555                 560

Pro Arg Ser Ser Ser Asn Ile Thr Leu Glu Tyr Ser Gly Met Asn Ser
            565                 570                 575

Ser Val Glu Ile Lys Gln Ala Asp Val Thr Leu Met Val Tyr Pro Leu
            580                 585                 590

Gly Tyr Ile Asn Asp Glu Ser Ile Leu Asn Asn Ala Ile Lys Asp Leu
            595                 600                 605

Tyr Tyr Tyr Ser Glu Arg Gln Ser Ala Ser Gly Pro Ala Met Thr Tyr
            610                 615                 620

Pro Val Phe Val Ala Ala Ala Gly Leu Leu Asn His Gly Ser Ser
625                 630                 635                 640

Ser Gln Ser Tyr Leu Tyr Lys Ser Val Leu Pro Tyr Leu Arg Ala Pro
            645                 650                 655

Phe Ala Gln Phe Ser Glu Gln Ser Asp Asp Asn Phe Leu Thr Asn Gly
            660                 665                 670

Leu Thr Gln Pro Ala Phe Pro Phe Leu Thr Ala Asn Gly Gly Phe Leu
            675                 680                 685

Gln Ser Ile Leu Phe Gly Leu Thr Gly Ile Arg Tyr Ser Tyr Glu Val
            690                 695                 700

Asp Pro Asp Thr Lys Lys Ile Asn Arg Leu Leu Arg Phe Asn Pro Ile
705                 710                 715                 720

Glu Leu Pro Leu Leu Pro Gly Gly Ile Ala Ile Arg Asn Phe Lys Tyr
            725                 730                 735

Met Asn Gln Val Leu Asp Ile Ile Asp Asp His Asn Gly Thr Ile
            740                 745                 750

Val His Lys Ser Gly Asp Val Pro Ile His Ile Lys Ile Pro Asn Arg
            755                 760                 765

Ser Leu Ile His Asp Gln Asp Ile Asn Phe Tyr Asn Gly Ser Glu Asn
            770                 775                 780

Glu Arg Lys Pro Asn Leu Glu Arg Arg Asp Val Asp Arg Val Gly Asp
785                 790                 795                 800

Pro Met Arg Met Asp Arg Tyr Gly Thr Tyr Tyr Leu Leu Lys Pro Lys
            805                 810                 815

Gln Glu Leu Thr Val Gln Leu Phe Lys Pro Gly Leu Asn Ala Arg Asn
            820                 825                 830

Asn Ile Ala Glu Asn Lys Gln Ile Thr Asn Leu Thr Ala Gly Val Pro
```

```
                    835              840              845
Gly Asp Val Ala Phe Ser Ala Leu Asp Gly Asn Asn Tyr Thr His Trp
    850              855              860

Gln Pro Leu Asp Lys Ile His Arg Ala Lys Leu Leu Ile Asp Leu Gly
865              870              875              880

Glu Tyr Asn Glu Lys Glu Ile Thr Lys Gly Met Ile Leu Trp Gly Gln
                885              890              895

Arg Pro Ala Lys Asn Ile Ser Ile Ser Ile Leu Pro His Ser Glu Lys
            900              905              910

Val Glu Asn Leu Phe Ala Asn Val Thr Glu Ile Met Gln Asn Ser Gly
        915              920              925

Asn Asp Gln Leu Leu Asn Glu Thr Ile Gly Gln Leu Leu Asp Asn Ala
    930              935              940

Gly Ile Pro Val Glu Asn Val Ile Asp Phe Asp Gly Ile Glu Gln Glu
945              950              955              960

Asp Asp Glu Ser Leu Asp Asp Val Gln Ala Leu Leu His Trp Lys Lys
                965              970              975

Glu Asp Leu Ala Lys Leu Ile Glu Gln Ile Pro Arg Leu Asn Phe Leu
            980              985              990

Lys Arg Lys Phe Val Lys Ile Leu  Asp Asn Val Pro Val  Ser Pro Ser
        995              1000              1005

Glu Pro  Tyr Tyr Glu Ala Ser  Arg Asn Gln Ser Leu  Ile Glu Ile
    1010              1015              1020

Leu Pro  Ser Asn Arg Thr Thr  Phe Thr Ile Asp Tyr  Asp Lys Phe
        1025              1030              1035

Ala Gly  Gly
    1040

<210> SEQ ID NO 5
<211> LENGTH: 804
<212> TYPE: DNA
<213> ORGANISM: Sequence cerevisiae
<220> FEATURE:
<221> NAME/KEY: CDS
<222> LOCATION: (1)..(801)

<400> SEQUENCE: 5 atg tcg aaa gct aca tat aag gaa cgt gct gct act cat cct agt cct      48
Met Ser Lys Ala Thr Tyr Lys Glu Arg Ala Ala Thr His Pro Ser Pro
1               5                   10                  15 gtt gct gcc aag cta ttt aat atc atg cac gaa aag caa aca aac ttg      96
Val Ala Ala Lys Leu Phe Asn Ile Met His Glu Lys Gln Thr Asn Leu
                20                  25                  30 tgt gct tca ttg gat gtt cgt acc acc aag gaa tta ctg gag tta gtt     144
Cys Ala Ser Leu Asp Val Arg Thr Thr Lys Glu Leu Leu Glu Leu Val
            35                  40                  45 gaa gca tta ggt ccc aaa att tgt tta cta aaa aca cat gtg gat atc     192
Glu Ala Leu Gly Pro Lys Ile Cys Leu Leu Lys Thr His Val Asp Ile
        50                  55                  60 ttg act gat ttt tcc atg gag ggc aca gtt aag ccg cta aag gca tta     240
Leu Thr Asp Phe Ser Met Glu Gly Thr Val Lys Pro Leu Lys Ala Leu
65                  70                  75                  80 tcc gcc aag tac aat ttt tta ctc ttc gaa gac aga aaa ttt gct gac     288
Ser Ala Lys Tyr Asn Phe Leu Leu Phe Glu Asp Arg Lys Phe Ala Asp
                85                  90                  95 att ggt aat aca gtc aaa ttg cag tac tct gcg ggt gta tac aga ata     336
Ile Gly Asn Thr Val Lys Leu Gln Tyr Ser Ala Gly Val Tyr Arg Ile
                100                 105                 110
```

```
gca gaa tgg gca gac att acg aat gca cac ggt gtg gtg ggc cca ggt      384
Ala Glu Trp Ala Asp Ile Thr Asn Ala His Gly Val Val Gly Pro Gly
        115                 120                 125 att gtt agc ggt ttg aag cag gcg gca gaa gaa gta aca aag gaa cct      432
Ile Val Ser Gly Leu Lys Gln Ala Ala Glu Glu Val Thr Lys Glu Pro
130                 135                 140 aga ggc ctt ttg atg tta gca gaa ttg tca tgc aag ggc tcc cta tct      480
Arg Gly Leu Leu Met Leu Ala Glu Leu Ser Cys Lys Gly Ser Leu Ser
145                 150                 155                 160 act gga gaa tat act aag ggt act gtt gac att gcg aag agc gac aaa      528
Thr Gly Glu Tyr Thr Lys Gly Thr Val Asp Ile Ala Lys Ser Asp Lys
                165                 170                 175 gat ttt gtt atc ggc ttt att gct caa aga gac atg ggt gga aga gat      576
Asp Phe Val Ile Gly Phe Ile Ala Gln Arg Asp Met Gly Gly Arg Asp
            180                 185                 190 gaa ggt tac gat tgg ttg att atg aca ccc ggt gtg ggt tta gat gac      624
Glu Gly Tyr Asp Trp Leu Ile Met Thr Pro Gly Val Gly Leu Asp Asp
        195                 200                 205 aag gga gac gca ttg ggt caa cag tat aga acc gtg gat gat gtg gtc      672
Lys Gly Asp Ala Leu Gly Gln Gln Tyr Arg Thr Val Asp Asp Val Val
    210                 215                 220 tct aca gga tct gac att att att gtt gga aga gga cta ttt gca aag      720
Ser Thr Gly Ser Asp Ile Ile Ile Val Gly Arg Gly Leu Phe Ala Lys
225                 230                 235                 240 gga agg gat gct aag gta gag ggt gaa cgt tac aga aaa gca ggc tgg      768
Gly Arg Asp Ala Lys Val Glu Gly Glu Arg Tyr Arg Lys Ala Gly Trp
                245                 250                 255 gaa gca tat ttg aga aga tgc ggc cag caa aac taa                       804
Glu Ala Tyr Leu Arg Arg Cys Gly Gln Gln Asn
            260                 265

<210> SEQ ID NO 6
<211> LENGTH: 267
<212> TYPE: PRT
<213> ORGANISM: Sequence cerevisiae

<400> SEQUENCE: 6

Met Ser Lys Ala Thr Tyr Lys Glu Arg Ala Ala Thr His Pro Ser Pro
1               5                   10                  15

Val Ala Ala Lys Leu Phe Asn Ile Met His Glu Lys Gln Thr Asn Leu
            20                  25                  30

Cys Ala Ser Leu Asp Val Arg Thr Thr Lys Glu Leu Leu Glu Leu Val
        35                  40                  45

Glu Ala Leu Gly Pro Lys Ile Cys Leu Leu Lys Thr His Val Asp Ile
    50                  55                  60

Leu Thr Asp Phe Ser Met Glu Gly Thr Val Lys Pro Leu Lys Ala Leu
65                  70                  75                  80

Ser Ala Lys Tyr Asn Phe Leu Leu Phe Glu Asp Arg Lys Phe Ala Asp
                85                  90                  95

Ile Gly Asn Thr Val Lys Leu Gln Tyr Ser Ala Gly Val Tyr Arg Ile
            100                 105                 110

Ala Glu Trp Ala Asp Ile Thr Asn Ala His Gly Val Val Gly Pro Gly
        115                 120                 125

Ile Val Ser Gly Leu Lys Gln Ala Ala Glu Glu Val Thr Lys Glu Pro
    130                 135                 140

Arg Gly Leu Leu Met Leu Ala Glu Leu Ser Cys Lys Gly Ser Leu Ser
145                 150                 155                 160
```

-continued

```
Thr Gly Glu Tyr Thr Lys Gly Thr Val Asp Ile Ala Lys Ser Asp Lys
            165                 170                 175

Asp Phe Val Ile Gly Phe Ile Ala Gln Arg Asp Met Gly Gly Arg Asp
            180                 185                 190

Glu Gly Tyr Asp Trp Leu Ile Met Thr Pro Gly Val Gly Leu Asp Asp
            195                 200                 205

Lys Gly Asp Ala Leu Gly Gln Gln Tyr Arg Thr Val Asp Asp Val Val
210                     215                 220

Ser Thr Gly Ser Asp Ile Ile Ile Val Gly Arg Gly Leu Phe Ala Lys
225                     230                 235                 240

Gly Arg Asp Ala Lys Val Glu Gly Glu Arg Tyr Arg Lys Ala Gly Trp
            245                 250                 255

Glu Ala Tyr Leu Arg Arg Cys Gly Gln Gln Asn
            260                 265
```

DRYING-RESISTANT, PRACTICAL BAKER'S YEAST

DETAILED DESCRIPTION OF THE INVENTION

1. Technical Field of the Invention

The present invention relates to extremely excellent, drying-resistant practical baker's yeast. Some types of drying-resistant baker's yeast have heretofore been produced. For their forms as commercial products, they are of so-called dry yeast, and are suitable to long-term storage. However, only two types of dry yeast are commercially available, of which (1) one is for baked goods having a relatively low sugar concentration (for example, French bread, etc.), and (2) the other is for high-sugar dough (for example, for sweetened buns, etc.) having a relatively high sugar concentration. Baked goods as produced with the dry yeast of those types are not characterized by their tastes. For its use in dough, the conventional dry yeast is selected merely depending on the sugar concentration in dough as roughly classified into two, high-sugar dough and low-sugar dough, since its ability to expand the dough is relatively high in the selected condition. The yeast of the invention is characterized not only by its strong power to ferment dough having specific sugar concentrations but also by its ability to give baked goods having characteristic and delicious tastes. Specifically, the yeast of the invention has good drying resistance while retaining the properties of practical baker's yeast. According to the invention, therefore, there are provided many dry yeast products which are useful in backing having good storability To that effect, the drying-resistant practical baker's yeast of the invention is extremely excellent.

Specifically, according to the invention in which is employed a novel constitution of merely inactivating only either one of the ATH1 gene or the NTH1 gene in practical baker's yeast having various excellent characteristics but not having resistance to drying, it has become possible to make the practical baker's yeast have drying resistance that is comparable to or higher than that of ordinary commercially-available baker's yeast for dry yeast. Therefore, the invention makes it possible to provide dry yeast having good storability and suitable to any baking methods for producing various types of baked goods, and the invention greatly contributes to developments in the baking industry.

2. Prior Art

For its commercial products, drying-resistant baker's yeast is produced in the form of so-called dry yeast. Commercial products of dry baker's yeast may be classified into two, depending on their production methods and properties. One is so-called active dry yeast that does not require any special apparatus for its production. This has a water content of around 10% and is generally granular, and its life for storage is relatively short. In its use, it is dissolved in warm water containing sugar, re-activated therein for ten minutes, and mixed with dough. The other is so-called instant dry yeast. This has a water content of around 4% and is storable for a long period of time (for example, for a few years in vacuum packages). In its use, it is once dissolved in warm water for re-hydration, and immediately mixed with dough without being intentionally re-activated, or it may be directly mixed with dough without being re-hydrated.

However, as so mentioned hereinabove, the conventional dry baker's yeast has a few variations. Given that situation, it is strongly desired in the art to develop excellent practical baker's yeast having good drying resistance and retaining the properties of ordinary baker's yeast (therein, the property of rapid expanding dough to give baked goods having good tastes and pleasant to the tongue).

The drying resistance as referred to herein is meant to indicate the characteristic especially indispensable to the strains to be used for producing the instant dry yeast of dry baker's yeast mentioned above. Specifically, the drying resistance is the ability of those strains to well grow in industrial cultivation conditions of fed-batch culture and to be well dried in particular industrial drying method of fluidized-bed drying to give dry yeast. In addition, the dry yeast must be well stored long, and immediately after re-hydrated with water, it must have the ability to well expand dough.

We, the present inventors have previously succeeded in obtaining frozen dough-resistant and high-sugar dough-resistant, practical baker's yeast by increasing its trehalose retentiveness, and have filed patent applications for it (see Japanese Patent Application No. 8-297886 for NTH1 (neutral trehalase gene) disruption; Japanese Patent Application No. 9-352016 for ATH1 (acidic trehalase gene) disruption; the report of Takano, et al. of National Food Research Institute of the Ministry of Agriculture, Forestry and Fisheries of Japan, red in the Meeting of the Japanese Society for Food Science and Technology in 1997).

On the other hand, it was believed that baker's yeast could have drying resistance only when its trehalose content could be increased. For this, John Kim, et al. (of the California University) suggested trehalase gene disruption in baker's yeast (see Applied and Environmental Microbiology, Vol. 62, No. 5, 1996). However, they used laboratory strains in their studies, and nothing is suggested for the usefulness of the ATH1 gene disruption in practical baker's yeast. In other words, their studies were not confirmed in the practical baking industry, and at present, the industrial usefulness of the ATH1 gene-disrupted strain is not confirmed at all. In fact, even if its trehalose content is increased, baker's yeast could not get drying resistance only through the increase. This is because dried cells (for dry yeast) require trehalose as the energy source of reactivation when they are re-hydrated with water. Therefore, the laboratory strains having been so genetically manipulated through NTH1 gene a disruption that their neutral trehalase activity is 0 (zero) could not get drying resistance. For the same reasons, it cannot be believed at all that the laboratory strains naturally having a lower degree of NTH1 activity than that of practical strains and having been genetically manipulated for ATH1 gene disruption could still retain the trehalase activity that is necessary for re-activation of the dried cells with water only by the action of the NTH1 gene therein.

Where the yeast of *Saccharomyces cerevisiae* is used as practical baker's yeast, its source shall be a species of *Saccharomyces cerevisiae,* and, in addition, the yeast must satisfy various requirements needed in its practical use. For example, the indispensable requirements for the yeast are as follows: 1. In order to cultivate it on an industrial scale, the yeast must grow well in blackstrap molasses media that are generally used for mass-cultivating baker's yeast (that is, the growth rate of the yeast is high, and the yield thereof is large), the baker's yeast having grown in the media must be efficiently separated therefrom, and the efficiency in the dehydrating step in the process of forming the thus-separated baker's yeast into commercial products must be high (in that step, used is a specific device of a so-called dehydrator). 2. The products could keep the yeast activity (dough-expanding activity) during long-term cold storage (generally, for a few weeks), they are hardly softened during the storage, they are white without adsorbing blackstrap molasses. Apart from those, the yeast is required to have capabilities compatible with various baking methods.

For the reasons noted above, there is almost no possibility that laboratory strains not subjected to the screening for practical baker's yeast could be directly used as those for practical baker's yeast. In general, the requirements noted above are rarely governed by one gene but are often defined by a plurality of genes. In addition, there are known few studies relating to the relationship between the properties of practical baker's yeast and the genes constituting the yeast.

Being different from laboratory strains, most strains for practical baker's yeast are polyploidal and hardly form spores. Therefore, even the application of the breeding method of mating/spore separation that is based on classic breeding systems and is generally applied to laboratory strains, to baker's yeast strains is extremely difficult. Good practical baker's yeast shall exclusively rely on the screening of spontaneous mutants from ordinary strains that have been practically used in the art for many years, or on the screening thereof from the natural world. Gunge, et al. first applied a classic breeding method to baker's yeast in their rare-mating method (see Genetics, Vol. 70, 1972), and after that, one example of practical application of the method was first described in the specification of a patent application filed in 1982 for "Saccharomyces species FD612" (see JP-B-1-16155).

Problems to be Solved by the Invention

As has been so mentioned hereinabove, dry baker's yeast has a few variations. This is because screening of strains for drying-resistant yeast requires much labor since it is not clarified as yet as to what factor in yeast cells governs the drying resistance of yeast. In fact, therefore, to obtain dry baker's yeast for practical use, yeast cells must be cultivated by fed-batch culture to make them have a suitable degree of fermenting power and a suitable trehalose content, and thereafter the thus-cultivated cells must be subjected to a dryability test using a fluidized-bed drying device comparable to an industrial one. Few attempts have heretofore been made in the art to breed strains for dry baker's yeast through mating.

Given that situation, we, the present inventors have specifically noted trehalose of various stress-related substances in yeast cells and have made various studies relating to the intracellular trehalose content of yeast cells. In particular, we attempted to increase the intracellular trehalose which acts as a protective substance when yeast cells are dried and which is to be the energy source when the dry baker's yeast of the dried cells is re-hydrated with water, and have completed the invention as a result of such our studies.

Means for Solving the Problems

Even though baker's yeast that is hardly killed by drying could be constructed through NIH1 or ATH1 gene disruption, drying-resistant practical baker's yeast capable of producing delicious bread could not be obtained as yet. We, the present inventors desired to modify practical baker's yeast having excellent properties but not having resistance to drying into drying-resistant practical baker's yeast still having its original excellent properties and additionally having drying resistance that is comparable to or higher than that of ordinary, commercially-available drying-resistant yeast. For this purpose, we analyzed in detail starting yeast strains, dry yeast from the strains and even final bread as produced by the use of the dry yeast in various experiments and, as a result, have completed the invention.

The invention relates to a set of NTH1 gene-disrupted, haploid yeasts as produced through gene manipulation of disrupting the NTH1 gene in a set of haploid yeasts of which the original hybridized diploid is practical baker's yeast.

The invention also relates to a diploid or higher polyploid, drying-resistant, practical baker's yeast as produced through mating with one or more NTH1 gene-disrupted, haploid yeasts produced through gene manipulation of disrupting the NTH1 gene in a haploid yeast of which the diploid is practical baker's yeast.

The invention further relates to a set of ATH1 gene-disrupted, haploid yeasts as produced through gene manipulation of disrupting the ATH1 gene in a set of haploid yeasts of which the original hybridized diploid is practical baker's yeast.

The invention still further relates to a diploid or higher polyploid, drying-resistant, practical baker's yeast as produced through mating with one or more ATH1 gene-disrupted, haploid yeasts produced through gene manipulation of disrupting the ATH1 gene in a haploid yeast of which the diploid is practical baker's yeast.

BRIEF DESCRIPTION OF THE DRAWINGS

FIG. 1 shows a part of the base sequence of NTH1 gene.

FIG. 2 shows another part of the base sequence of the gene that follows the part of FIG. 1.

FIG. 3 shows still another part of the base sequence of the gene that follows the part of FIG. 2.

FIG. 4 shows still another part of the base sequence of the gene that follows the part of FIG. 3.

FIG. 7 shows the confirmation of NTH1 gene disruption.

FIG. 10 shows the confirmation of ATH1 gene disruption, in which the lane 1 indicates a DNA molecular weight marker, the lanes 2, 4, 6 and 8 indicate PCR products of DNA derived from strains 7, 21, 18 and 19, respectively, and the lanes 3, 5, 7 and 9 indicate PCR products of DNA derived from strains 7dA, 21dA, 18dA and 19dA, respectively.

Figure 5:
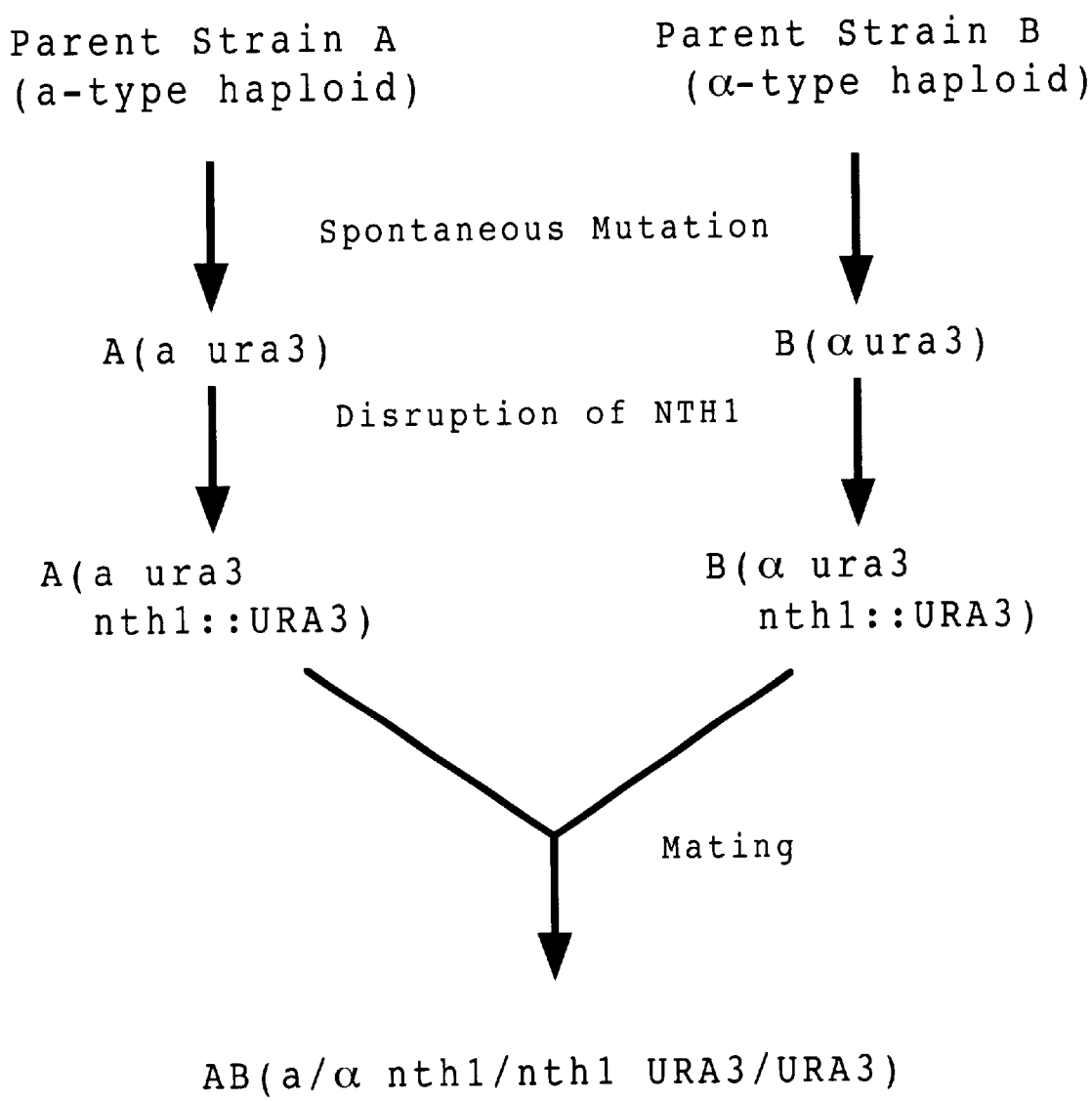
FIG. 5 shows a process of constructing a diploid, drying-resistant practical baker's yeast through mating with NTH1 gene-disrupted haploid yeast cells.

MODES OF CARRYING OUT THE INVENTION 1. (Screening for Haploid Yeasts of Which the Diploids are Practical Baker's Yeasts, and Genetic Marking)

In the invention, the screening of yeast strains for those to be subjected to gene manipulation is indispensable. First are selected haploid yeast strains, which must be identified as to whether they are a-type ones or α-type ones. Where a selected haploid yeast could be conjugated with a previously prepared a-type haploid yeast within a few hours in the culture of the two in a ratio of 1/1 and where the conjugation could be confirmed with a microscope, the haploid yeast is identified as an a-type one. On the other hand, where the conjugation of a selected haploid yeast with a previously prepared a-type haploid yeast in the culture of the two in a ratio of 1/1 could be confirmed, the haploid yeast is identified as an α-type one. In laboratory experiments, the thus-identified haploid yeasts could be subjected to the next step of genetic marking. In constructing practical baker's yeasts, however, a step of screening the identified haploid yeasts is indispensable prior to the genetic marking step. The screening step may be effected in the manner mentioned below.

An a-type or α-type haploid yeast is mated with an α-type or a-type haploid to construct an a/α-type diploid yeast. Then, in the first stage, the resulting diploid strains are screened in a mass-cultivation test such as that mentioned hereinabove, which is based on the possibility of industrial production of the strains. Next, in the second stage, the strains thus cultivated and screened in the previous test are further screened for those that satisfy the requirements of commercial products also mentioned hereinabove. Finally, the strains thus passed the two-stage screening are cultivated, and the thus-cultivated strains are used in producing different types of bread. In this final step, the strains with which excellent bread samples were produced are selected. Thus, the yeasts used in preparing the excellent bread samples are known, and they are determined to be haploid yeasts to be subjected to gene manipulation. There are various types of bread, including, for example, loaves, rolls, croissants, French bread and rolls, and buns, for all of which diploid yeasts as constructed from various haploid yeasts are tested. Depending on the haploid yeast to be mated, the characteristics of the bread to be prepared by dough that comprises the mated diploid yeast greatly vary. Therefore, the screening for the suitable haploid yeast to be subjected to gene manipulation is extremely difficult. However, in order to obtain the intended, drying-resistant practical baker's yeast, this screening step is indispensable.

Gene manipulation of yeast requires genetic markers. Practical baker's yeast has no marker, and where it is subjected to gene manipulation, employable are markers except those for the genes of the yeast, such as chemical-resistant markers and the like, which, however, are unfavorable from the viewpoint of the safety in the gene manipulation. Haploid strains to be subjected to gene manipulation within the range of their self-cloning require genetic markers. In that case, if the yeast to be processed is mutated with chemicals or the like, it will lose its intrinsic favorable properties. For this, therefore, it is desirable to employ a screening method for spontaneous mutants. For example, as the marker genes, preferred are URA3, LYS2, ADE2 and the like for easy screening for the intended defective strains.

To introduce a gene marker, ura3 (URA3-defective strain) into a haploid strain, cells of the strain are screened in a 5-fluoro-orotic acid-containing medium. Briefly, cells of a haploid strain are cultivated in a YPD liquid medium, centrifuged, and washed with a 0.85% NaCl solution. About $10^8$ cells thus cultivated are applied onto a 5-fluoro-orotic acid-containing medium (0.7% YEAST NITROGEN BASE (DIFCO), 2% glucose, 0.1% 5-fluoro-orotic acid, 0.05% uracil, 2% agar) and cultivated thereon at 30° C. for 3 days, and the cells growing on the medium to give colonies thereon are selected. The cells having grown on the medium do not have intact URA3 gene, as having been spontaneously mutated. Such URA3-defective cells are obtained at a frequency of one cell per $10^6$ to $10^7$ cells.

Those URA3-defective cells could not grow on an uracil-free medium, but could grow thereon only after having been transformed with an URA3-containing plasmid, such as YCp50 or the like. Therefore, through the transformation of those cells, the defect of URA3 therein can be confirmed.

2. (Formation of NTH1 Gene-disrupted Strain)

In the invention, where a marker gene, such as URA3 (uridylic acid synthetase) (Gene 29: 113–124, (1984)), ADE2, LYS2 or the like, is inserted into the NTH1 gene (neutral trehalase gene) (J.B.C. 268: 4766–4774 (1993)) of a haploid yeast, which is shown in FIG. 1, FIG. 2, FIG. 3 and FIG. 4, the NTH1 gene is disrupted and could no more be expressed in the NTH1 gene. In the resulting yeast with the NTH1 gene disrupted, the URA3 or other auxotrophic marker gene as inserted into the yeast is expressed, whereby the disruption of the NTH1 gene in the yeast is confirmed. The URA3 and other marker genes to be inserted into the yeast are preferably those derived from *Saccharomyces cerevisiae*, especially those from baker's yeast, for realizing their self-cloning.

The object of the disruption of the NTH1 gene in haploid yeasts is to prevent the NTH1 gene from being expressed in the yeasts to give a neutral trehalase which decomposes trehalose. For this, therefore, all or a part of the gene sequence of the NTH1 gene is deleted. Preferably, in the invention, URA3 is inserted entirely or partly into the region of the NTH1 gene of a haploid yeast to thereby destruct the NTH1 gene therein.

First, a part of the gene sequence of the NTH1 gene shown in FIG. 1, FIG. 2, FIG. 3 and FIG. 4 is inserted into an *E. coli* vector, such as pUC19, then the URA3 gene having a base sequence of Sequence Number 4 in the Sequence Listing mentioned below is inserted into the partial region of the NTH1 gene in the vector. The resulting placid is proliferated in *E. coli* cells. From this plasmid, cleaved out is only the DNA fragment of NTH1 (former half)-URA3-NTH1 (latter half). The thus-isolated DNA fragment is thereafter transformed into a haploid yeast, of which the diploid is a practical baker's yeast, in a lithium acetate method.

The DNA fragment, NTH1 (former half)-URA1-NTH1 (latter half) in the haploid yeast is hybridized and recombined in such a manner that URA3 still remains in a part or entire region of the NTH1 gene sequence whereby the NTH1 gene is completely divided into two, its former half and latter half, via URA3 therebetween, to complete the gene disruption.

3. (Mating of NTH1 Gene-disrupted Haploid Yeast)

The NTH1 gene-disrupted haploid yeast obtained herein is either an a-type or α-type one, while having such necessary properties that its diploid yeast can be a practical baker's yeast. In other words, only the NTH1 gene is disrupted in the haploid yeast through the gene disruption, while the other genes in the resulting NTH1 gene-disrupted haploid yeast are intact and still maintain their intrinsic properties.

In the invention, one or more NTH1 gene-disrupted haploid yeasts as prepared through the process of disrupting the NTH1 gene of a haploid yeast, of which the diploid is a practical baker's yeast, are mated with any other haploid yeasts to give diploid or higher polyploid, drying-resistant practical baker's yeasts.

One preferred embodiment of the mating is to mate an a-type, NTH1 gene-disrupted haploid yeast is mated with an a type, NTH1 gene-disrupted haploid yeast to give a diploid yeast.

FIG. 5 shows an outline of the process of producing the diploid, drying-resistant practical baker's yeast of the invention. One of many diploid, drying-resistant practical baker's yeasts obtained herein, a baker's yeast of Saccharomyces cerevisiae T154 (FERM BP-5678) was deposited in the National Institute of Bioscience and Human-Technology, Agency of Industrial Science and Technology of Japan.

The polyploid, drying-resistant practical baker's yeasts of the invention have excellent drying resistance. In particular, when they are cultivated on an industrial scale and are dried also on an industrial scale to give instant dry yeasts for bread production, the power of the resulting dry yeasts for dough fermentation is extremely great.

4. (Cloning of Acidic Trehalase Gene)

Cloning of acidic trehalase gene ATH1 may be attained for example, in an ordinary shot-gun cloning method based on the fact that ATH1 gene-defective strains could not grow in a medium comprising trehalose as only one carbon source. However, since the full-length base sequence of the chromosome of the yeast of Saccharomyces cerevisiae was already known, the cloning of the gene of which the sequence was already known such as the acidic trehalase gene ATH1 is generally effected through PCR (polymerase chain reaction). For inactivating (disrupting) the gene, cloning of the full-length gene is unnecessary, and a partial region of the gene may be cloned.

5. (Construction of Vector for ATH1 Gene Disruption, and Disruption of ATH1 Gene)

The object of the disruption of the ATH1 gene in haploid yeasts is to prevent the AH1 gene from being expressed in the yeasts to give an acidic trehalase which decomposes trehalose. For this, therefore, all or a part of the gene sequence of the ATH1 gene is deleted. Preferably, in the invention, the ATH1 gene in a haploid yeast is completely replaced with URA3, or URA3 is inserted into the ATH1 gene thereby substantially inactivating the ATH1 gene for disrupting the gene in the yeast.

First, a part of the amino acid-coding region of the ATH1 gene of Sequence Number 3 in the Sequence Listing is, after having been amplified through PCR, inserted into an E. coli vector, such as pGEM-T, then the full-length URA3 gene of Sequence Number 4 is inserted into the partial region of the ATH1 gene in the vector. The resulting plasmid is proliferated in E. coli cells. From this plasmid, cleaved out is only the DNA fragment of ATH1 gene (former half)-URA3-ATH1 gene (latter half). With the thus-isolated DNA fragment, thereafter transformed is a haploid yeast, of which the diploid is a practical baker's yeast, by a lithium acetate method. The DNA fragment, ATH1 gene (former half)-URA3-ATH1 gene (latter half) in the haploid yeast is site-specifically recombined with the ATH1 gene in the yeast, whereby the ATH1 gene is completely divided into two, its former half and latter half, via URA1 therebetween, resulting in that the gene is completely disrupted and is substantially inactivated.

6. (Formation of Diploid)

The ATH1 gene-disrupted haploid yeast obtained herein is either an a-type or α-type one, while having such necessary properties that its diploid yeast can be a practical baker's yeast. In other words, only the ATH1 gene is disrupted in the haploid yeast through the gene disruption, while the other genes in the resulting ATH1 gene-disrupted haploid yeast are intact and still maintain their intrinsic properties. In the invention, one or more ATH1 gene-disrupted haploid yeasts as prepared through the process of disrupting the ATH1 gene of a haploid yeast, of which the diploid is a practical baker's yeast, are mated with any other haploid yeasts to give diploid or higher polyploid, drying-resistant practical baker's yeasts.

EXAMPLE 1

(Screening for Haploid Yeast of Which the Diploid is Practical Baker's Yeast)

25 stock cultures of wild haploid yeasts were identified as to whether they are a-type ones or α-type ones, and all of these were tested to know as to whether or not their diploids could be practical baker's yeasts. As a result of the test, 8 strains as in Table 15 were selected.

These 8 strains were subjected to NTH1 gene disruption according to the method mentioned below, by which the NTH1 gene existing therein was disrupted. Before and after the gene disruption, the neutral trehalase activity of each strain was measured.

The data obtained are shown in Table 15, from which it was confirmed that the neutral trehalase activity of the NTH1 gene-disrupted strains was significantly lowered. That is, the data indicate the disruption of the NTH1 gene in those strains.

TABLE 15

Comparison between the NTH activity of haploid yeast strains (wild strains), of which the diploids are practical baker's yeasts, and that of NTH1 gene-disrupted strains

| | NTH (spec. act., mU/mg protein) | |
|---|---|---|
| Strain No. and Its Type | Wild | Δnth |
| 2(a) | 93 | 4 |
| 7(a) | 87 | 6 |
| 12(α) | 83 | 3 |
| 13(α) | 12 | 0 |
| 14(a) | 64 | 3 |
| 18(α) | 75 | 1 |
| 19(α) | 39 | 1 |
| 21(a) | 18 | 0 |

(NTH1 Gene to be Disrupted)

It is known that NTH1 gene is positioned just adjacent to the centromere in the fourth chromosome of Saccharomyces cerevisiae of baker's yeast, and its gene sequence is as in FIG. 1, FIG. 2, FIG. 3 and FIG. 4.

In the invention, the NTH1 gene of baker's yeast was obtained from the region containing the centromere in the fourth chromosome of a usually-available yeast vector, YCp50 through gene eviction, and its sequence was confirmed as in FIG. 1, FIG. 2, FIG. 3 and FIG. 4.

Figure 6:
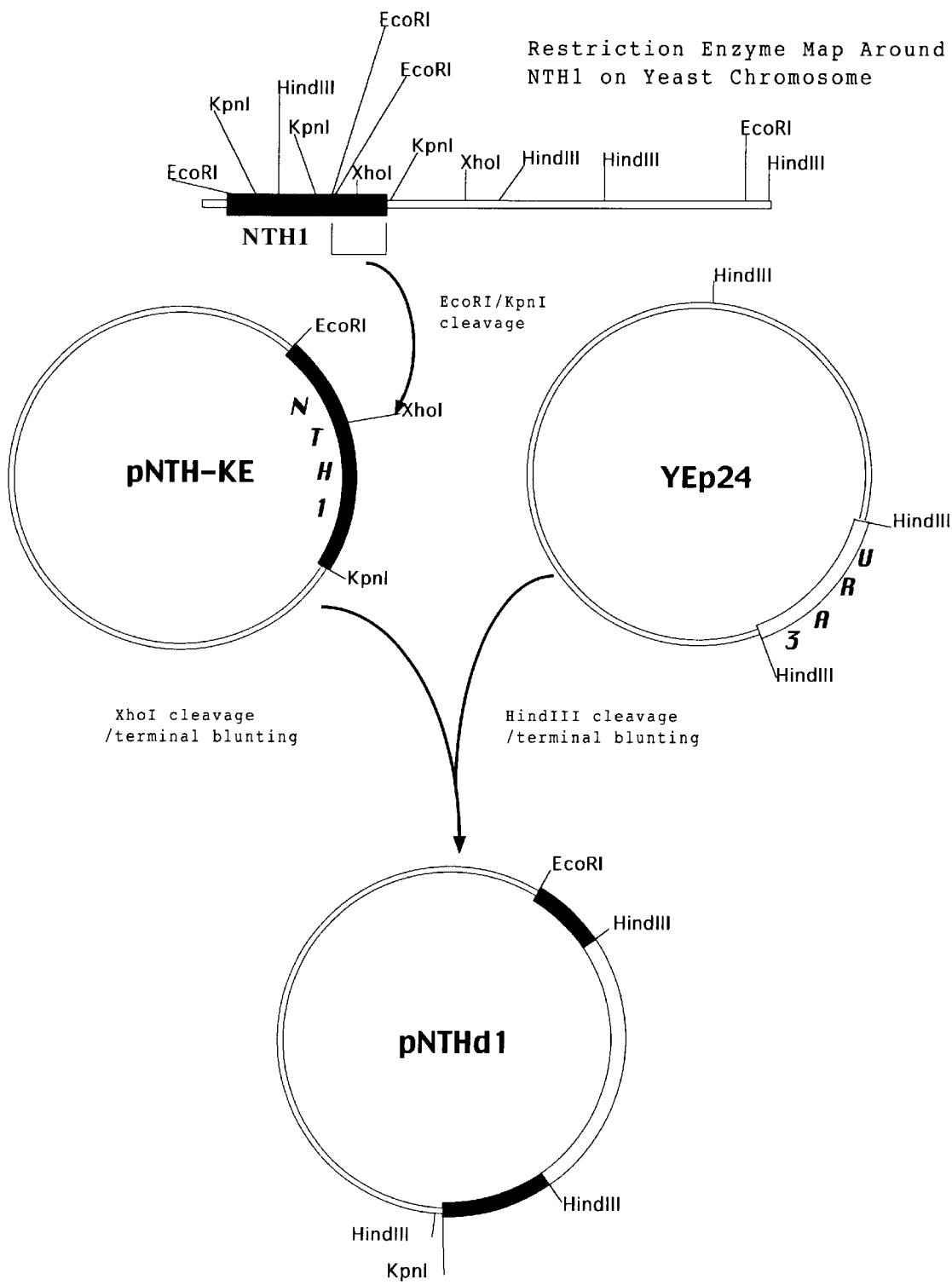
FIG. 6 shows a process of constructing a vector for NTH1 gene disruption.

(Construction of Vector for Disrupting NTH1 Gene)

pNTHd1:

From the NTH1 gene cloned, pNTHd1 was constructed as in FIG. 6.

Precisely, the region of NTH1 gene between the KpnI-recognition site in the 3'-side and the EcoRI-recognition site in the upstream site above it, which was about 770 bp, was cleaved at the both recognition sites, as in FIG. 6, and the resulting fragment was inserted into a commercially-available E. coli vector, pUC19, at the same restriction enzyme-recognition sites (KpnI and EcoRI-recognition sites) to obtain pNTH-KE. The resulting plasmid was cleaved at the XhoI-recognition site, and its terminals were blunted with a DNA polymerase. On the other hand, the URA3 gene in commercially-available YEp24, which is as in FIG. 6, was cleaved with HindIII and recovered. This U fragment of about 1,170 bp was blunted with a DNA polymerase, and inserted into the plasmid pNTH-KE having been cleaved and blunted as above, through ligation with a ligase to obtain pNTHd1.

(Disruption of NTH1 Gene of Haploid Yeast)
Disruption of NTH1 Gene with pNTHd1:

pNTHd1 was cleaved with EcoRI and KpnI to isolate a DNA fragment of NTH1 (former half)-URA3-NTH1 (latter half), with which each haploid yeast of No. 2, No. 7, No. 12, No. 13, No. 14, No. 18, No. 19 and No. 21, all shown in Table 15, was transformed in a lithium acetate process.

The chromosomal DNA extracted from each of those transformant strains was digested with EcoRI, and 0.5 µg of the DNA fragment was subjected to agarose gel electrophoresis followed by Southern hybridization, from which was confirmed the gene disruption as in FIG. 7. In FIG. 7, the left side column indicates the position of the bands of the molecular weight markers (λDNA-HindIII digested).

Each lane corresponds to the strain number as follows: Lane 1 is No. 2; lane 2 is No. 2-d; lane 3 is No. 7; lane 4 is No. 7-d; lane 5 is No. 12; lane 6 is No. 12-d; lane 7 is No. 13; lane 8 is No. 13-d; lane 9 is No. 14; lane 10 is No. 14-d; lane 11 is No. 18; lane 12 is No. 18-d; lane 13 is No. 19; lane 14 is No. 19-d; lane 15 is No. 21; and lane 16 is No. 21-d. In those, "d" means that the strain was processed with pNTHd1 for gene disruption, and the same shall apply to the strains in other Tables. The data in FIG. 7 verify the disruption of the NTH1 gene in those strains.

EXAMPLE 2

(Screening for Haploid Yeast of Which the Diploid is Practical Baker's Yeast)

25 stock cultures of wild haploid yeasts were identified as to whether they are a-type ones or α-type ones, and all of these were tested to know as to whether or not their diploids could be practical baker's yeasts. As a result of the test, 8 strains as in Table 16 were selected. These 8 strains were subjected to ATH1 gene disruption according to the method mentioned below, by which the ATH1 gene existing therein was disrupted. Before and after the gene disruption, the acidic trehalase activity of each strain was measured.

The data obtained are shown in Table 16, from which it was confirmed that the acidic trehalase activity of the ATH1 gene-disrupted strains was significantly lowered. That is, the data indicate the disruption of the ATH1 gene in those strains.

TABLE 16

Comparison between the ATH activity of haploid yeast strain (wild strain), of which the diploid is practical baker's yeast, and that of ATH1 gene-disrupted strain

| Sample | Acidic Trehalase Activity (mU/mg protein) |
| --- | --- |
| 2 (ATH1) | 6.13 |
| 2dA (ath1) | 0.20 |
| 7 (ATH1) | 4.96 |
| 7dA (ath1) | 0.25 |
| 14 (ATH1) | 8.55 |
| 14da (ath1) | 0.18 |
| 21 (ATH1) | 5.14 |
| 21dA (ath1) | 1.31 |
| 12 (ATH1) | 9.01 |
| 12dA (ath1) | 0.82 |
| 13 (ATH1) | 6.22 |
| 13dA (ath1) | 0.06 |
| 18 (ATH1) | 8.55 |
| 18dA (ath1) | 1.36 |
| 19 (ATH1) | 9.06 |
| 19dA (ath1) | 0.67 |

(Cloning of ATH1 Gene)

Figure 8:
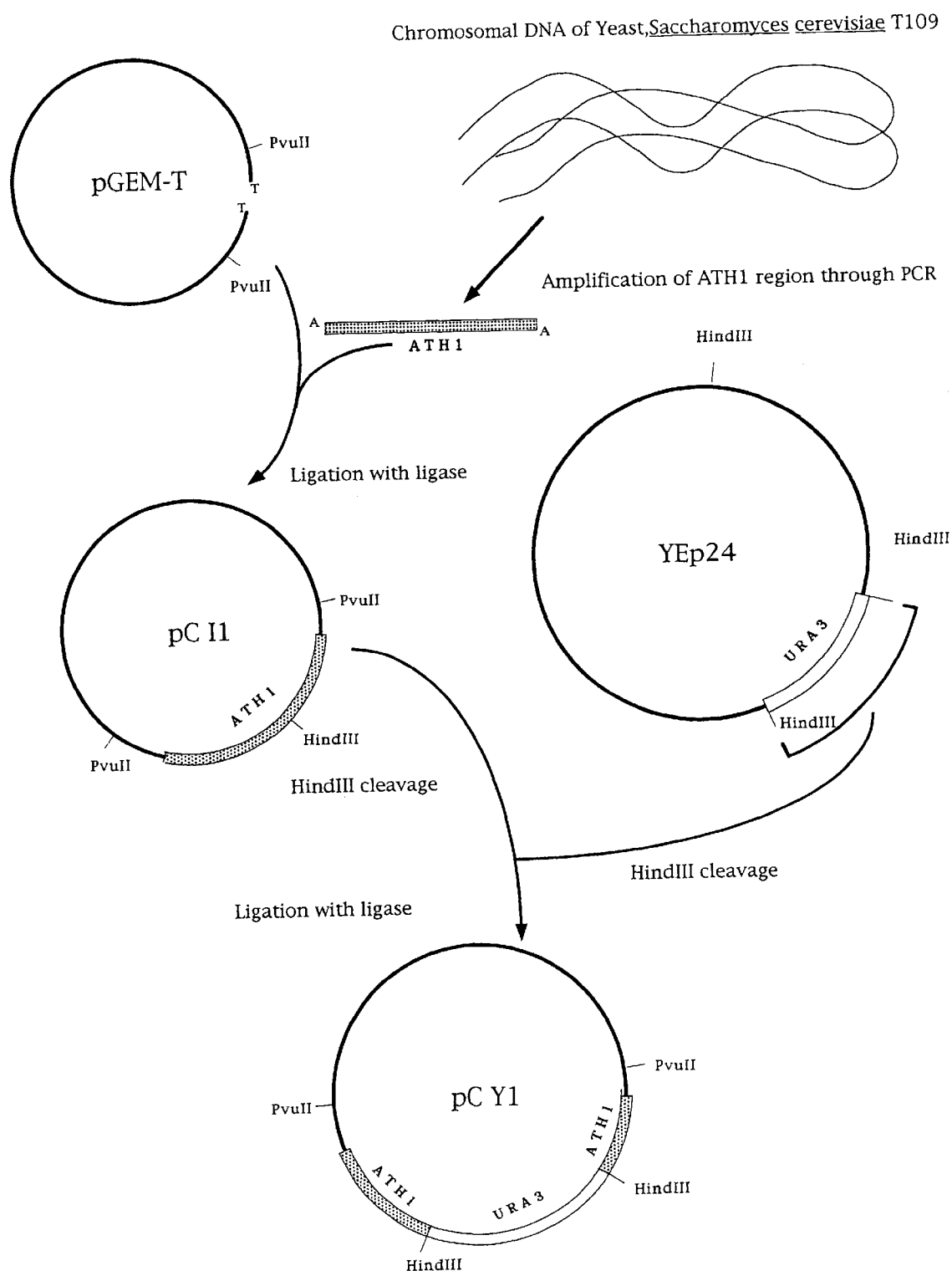
FIG. 8 shows a process of constructing a vector for ATH1 gene disruption.

A partial sequence of ATH1 gene was cloned, using a Promega's pGEM-T vector system. The outline of the cloning is shown in FIG. 8.

Precisely, based on the known base sequence of ATH1 gene (see Yeast, Vol. 11, 1995), 20 bp primers of Sequence Number 1 and Sequence Number 2 were designed in an ordinary manner. A chromosomal DNA was extracted from the yeast of Saccharomyces cerevisiae T019, and purified. Using this DNA as the template, along with the synthetic DNA primers of Sequence Numbers 1 and 2 noted above, a partial sequence of 1,150 base pairs between the 481st base and the 1,630th base in the coding region for ATH1 gene was amplified through PCR. Next, the thus-amplified DNA fragment was purified in an ordinary manner, and ligated with a pGEM-T vector by the use of a T4 DNA ligase. Thus was obtained a plasmid pCI1. This plasmid pCI1 was introduced into cells of E. coli (transformation) in an ordinary manner, amplified, and purified. Next, the restriction enzyme HindIII-recognition site, which is only one in the ATH1 gene partial sequence in the purified plasmid, was cleaved with the enzyme HindIII. On the other hand, a known plasmid YEp24 having URA3 gene was cleaved with the enzyme HindIII to isolate 1,166 bp DNA fragment containing the full-length of URA3 gene from it. After having been purified in an ordinary manner, the DNA fragment of URA3 gene was ligated with the HindIII-cleaved pCI1 by the use of the T4 DNA ligase to construct a plasmid pCY1 for ATH1 gene disruption.

(Formation of ATH1 Gene-disrupted Haploid)

According to the method mentioned hereinabove, an a-type haploid yeast (wild strain) was processed to be a strain of ura3, and then transformed with the DNA fragment comprising the ATH1 partial sequence and URA3, that had been cleaved with a restriction enzyme PvuII from the plasmid pCY1 (this is for ATH1 gene disruption) and was isolated and purified, according to a lithium acetate process. The non-transformed strain requires uracil in its growth, and the transformant was identified by its character not requiring uracil in its growth. In the same manner, an α-type haploid yeast (wild strain) was processed to be a strain of ura3 according to the method mentioned hereinabove. On the other hand, the plasmid pCY1 for ATH1 gene disruption was cleaved with a restriction enzyme PvuII, and the DNA fragment comprising the ATH1 partial sequence and URA3 was isolated and purified. The ura3 strain was transformed with this DNA according to a lithium acetate process. The non-transformed strain requires uracil in its growth, and the transformant was identified by its character not requiring uracil in its growth.

(Confirmation of ATH1 Gene Disruption)

Figure 9:
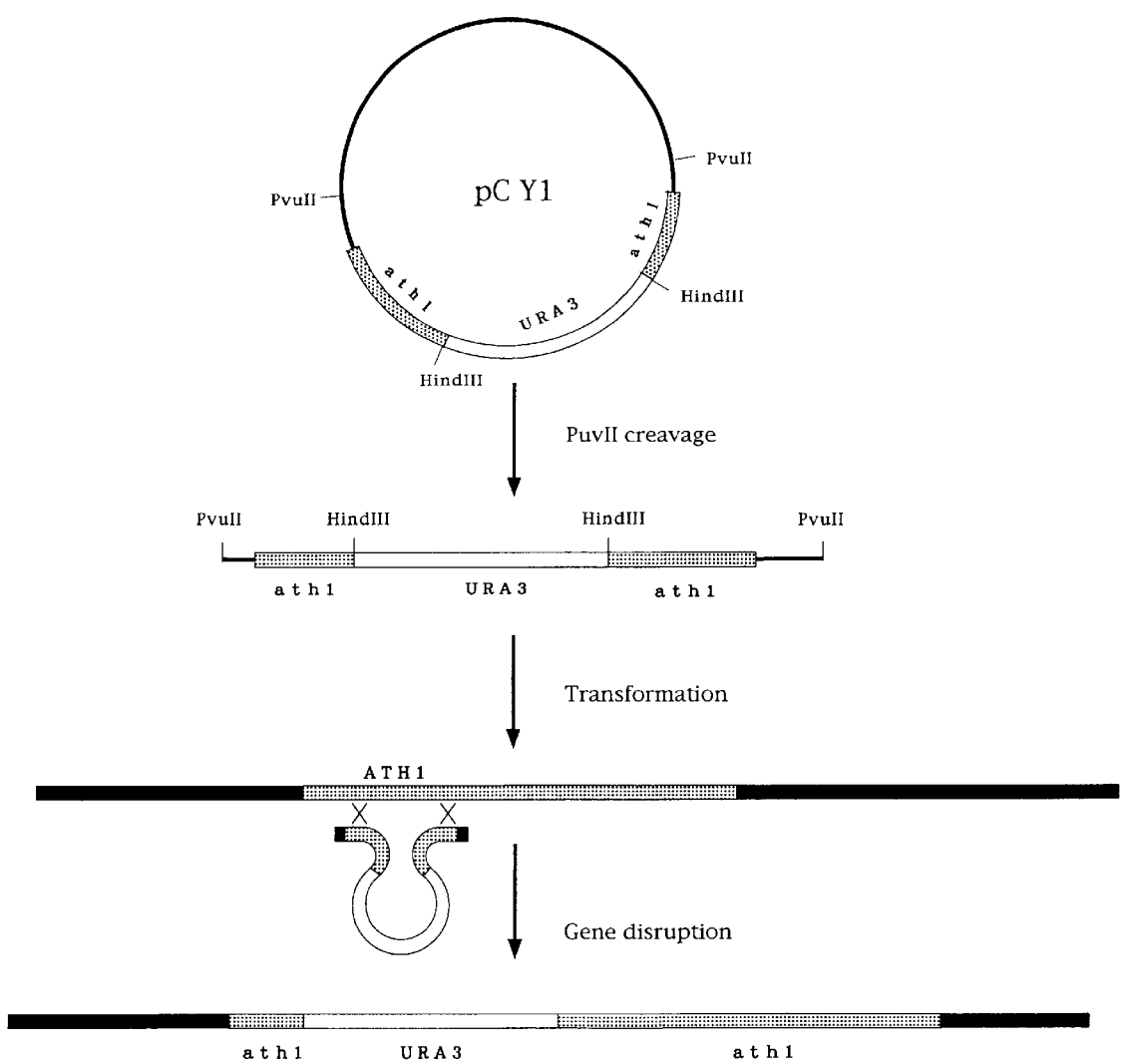
FIG. 9 is a conceptual view showing ATH1 gene disruption.

The ATH1 gene disruption was theoretically confirmed through PCR. Precisely, the total chromosomal DNA was extracted from both the wild strain and the gene-disrupted strain and each DNA was amplified with the primers of Sequence Number 1 and Sequence Number 2, and the thus-amplified DNAs were compared with each other with respect to their length. The data are shown in FIG. 9. Theoretically, the DNA fragment from the wild strain is amplified to have 1,150 bp, while that from the gene-disrupted strain is to have 2,316 bp. The theoretical data correspond to the data measured, as in FIG. 10, which supports the gene disruption.

(Confirmation of ATH1 Gene Inactivation)

To confirm the ATH1 gene disruption, the acidic trehalase activity of both wild strains (ATH1, in which the ATH1 gene is not disrupted) and ATH1 gene-disrupted strains (ath1) was measured. Precisely, 18-φ test tubes each charged with 5 ml of a YPD medium (1% yeast extract, 2% peptone, 2% glucose) were prepared, in which were separately inoculated platinum loop of cells of each wild strain and platinum loop of cells of each ATH1 gene-disrupted strain, and cultivated therein at 30° C. for 48 hours with shaking. The acidic trehalase activity of the thus-cultivated cells was measured in an ordinary manner. The data obtained are in Table 16. The acidic trehalase activity of the gene-disrupted strains was obviously lowered, as compared with that of the non-disrupted wild strains, and was nearly 0 (zero). This supports the ATH1 gene inactivation in the disrupted strains.

EXAMPLE 3
(Formation of NTH1 and ATH1 Genes-disrupted Strain)

Eight NTH1 gene-disrupted strains that were prepared according to the method of Example 1 do not require uracil in their growth. To again introduce the ura3 marker into them, these strains were cultivated on the 5-FOA-containing medium for spontaneous mutation, in the same manner as mentioned above. Of those, the mutant strains having grown in the medium were collected. In the mutant strains, the URA3 gene having been inserted thereinto in the process of NTH1 gene disruption was inactivated through spontaneous mutation. These strains were subjected to ATH1 gene disruption in the same manner as in Example 2. In the resulting strains, the ATH1 gene disruption and the ATH1 gene inactivation were confirmed in the same manner as in Example 2. The diploids of the strains are of practical baker's yeast.

EXAMPLE 4
(Mating of a-type Haploid Yeast and α-type Haploid Yeast)

The mating matrix 1 in the following Table 17 shows various combinations of wild strains and pNTHd1-processed strains.

TABLE 17

Mating Matrix 1

|  | 2 (a) | 7 (a) | 14 (a) | 21 (a) | 2d-1 (a) | 7d-1 (a) | 14d-1 (a) | 21d-1 (a) |
|---|---|---|---|---|---|---|---|---|
| 12 (α) | T101 | T102 | T103 | T104 | T105 | T106 | T107 | T108 |
| 13 (α) | T109 | T110 | T111 | T112 | T113 | T114 | T115 | T116 |
| 18 (α) | T117 | T118 | T119 | T120 | T121 | T122 | T123 | T124 |
| 19 (α) | T125 | T126 | T127 | T128 | T129 | T130 | T131 | T132 |
| 12d-1 (α) | T133 | T134 | T135 | T136 | T137 | T138 | T139 | T140 |
| 13d-1 (α) | T141 | T142 | T143 | T144 | T145 | T146 | T147 | T148 |
| 18d-1 (α) | T149 | T150 | T151 | T152 | T153 | T154 | T155 | T156 |
| 19d-1 (α) | T157 | T158 | T159 | T160 | T161 | T162 | T163 | T164 |

In Table 17, the strains in the uppermost row are all a-type ones, while those in the leftmost column are all α-type ones. In this, the strains with "d-1" are gene-disrupted ones as processed with pNTHd1; while those with no "d-1" are wild strains as in Table 15. Each one in the uppermost row in Table 17 was mated with each one in the leftmost column to obtain 64 diploid yeast strains, T101 through T164, in all as in Table 17.

The mating matrix 2 in Table 18 shows various combinations of wild strains and pCY1-processed, gene-disrupted strains. In Table 18, the strains in the uppermost row are all a-type ones, while those in the leftmost column are all α-type ones. In this, the strains with "d-A" are gene-disrupted ones as processed with pCY1; while those with no "d-A" are wild strains as in Table 16. Each one in the uppermost row was mated with each one in the leftmost column to obtain 64 diploid yeasts strains, T101 through T128 and A301 through A361, in all as in Table 18.

TABLE 18

Mating Matrix 2

|  | 2 (a) | 7 (a) | 14 (a) | 21 (a) | 2d-A (a) | 7d-A (a) | 14d-A (a) | 21d-A (a) |
|---|---|---|---|---|---|---|---|---|
| 12 (α) | T101 | T102 | T103 | T104 | A329 | A330 | A331 | A332 |
| 13 (α) | T109 | T110 | T111 | T112 | A333 | A334 | A335 | A336 |
| 18 (α) | T117 | T118 | T119 | T120 | A337 | A338 | A339 | A340 |
| 19 (α) | T125 | T126 | T127 | T128 | A341 | A342 | A343 | A345 |
| 12d-A (α) | A346 | A347 | A348 | A349 | A301 | A302 | A303 | A304 |
| 13d-A (α) | A350 | A351 | A352 | A353 | A309 | A310 | A311 | A312 |
| 18d-A (α) | A354 | A355 | A356 | A357 | A317 | A318 | A319 | A320 |
| 19d-A (α) | A358 | A359 | A360 | A361 | A325 | A326 | A327 | A328 |

The mating matrix 3 in Table 19 shows various combinations of pNTHd1 and pCY1-processed, NTH1 and ATH1 genes-disrupted strains. In Table 19, the strains in the uppermost row are all a-type ones, while those in the leftmost column are all α-type ones. The strains with "d-AT" in Table 19 were processed with pNTHd1 and pCY1, in which both the NTH1 gene and the ATH1 gene were disrupted. Each one in the uppermost row was mated with each one in the leftmost column to obtain 16 diploid yeasts strains in all, as in Table 19.

TABLE 19

Mating Matrix 3

|  | 2d-AT (a) | 7d-AT (a) | 14d-AT (a) | 21d-AT (a) |
|---|---|---|---|---|
| 12d-AT (α) | AT401 | AT402 | AT403 | AT404 |
| 13d-AT (α) | AT409 | AT410 | AT411 | AT412 |
| 18d-AT (α) | AT417 | AT418 | AT419 | AT420 |
| 19d-AT (α) | AT425 | AT426 | AT427 | AT428 |

The mating was effected as follows: First, a pair of a-type strain and α-type strain were separately cultivated and proliferated in YPD media at 30° C. for one day. Nearly the same number of the proliferated cells of the both strains were put into a fresh YPD medium and further cultivated therein at 30° C. for 12 hours. Then, the conjugated yeast cells were isolated, applied onto a YPD-agar medium, and cultivated thereon at 30° C. for 1 or 2 days. Relatively large colonies formed were taken out. It was confirmed that the cells in those colonies have no conjugating ability and that they are larger than the haploid cells through microscopic observation. Thus, the formation of diploid yeast cells was confirmed.

EXAMPLE 5

Cells of NTH1 gene-disrupted strains, ATH1 gene-disrupted strains and NTH1 and ATH1 genes-disrupted strains were cultivated, and checked for the trehalose content profile therein in the manner mentioned below.

(Cultivation of Diploid, Drying-resistant Practical Yeast Strains)

Cells of each diploid, drying-resistant practical yeast strain were cultivated in 30-liter jar fermenters under the condition mentioned below.

| 30-Liter jar culture | | |
|---|---|---|
| | Pre-Culture | Culture |
| Sugar Weight (as sucrose) | 1035 g | 1400 g |
| Urea | 103 g | 140 g |
| Monosodium phosphate dihydrate | 20.7 g | 28 g |
| Seed yeast (weight) | 20 g(*1) | 420 g(*2) |
| 30-Liter jar: | | |
| Maker: Oriental Bioservice KK | | |
| Name: Fermenter Control System MC-10 | | |
| Volume: 30 liters | | |
| Revolution of stirrer: 600 rpm | | |
| Aeration: 16 liters/min | | |

(*1)One platinum loop of yeast cells was inoculated in a 1-liter Sakaguchi flask charged with 250 ml of a YPD medium, and cultivated therein at 30° C. for 2 days. The cells of four flasks were used as the seed cells.
(*2)The cells grown in the pre-culture were taken out through centrifugation, and washed with deionized water. A part of those cells were used.

All the tested strains gave an yield of from 120 to 140%, relative to the weight of sugar, of the yield given by the commercially-available baker's yeast strain as cultivated in the same manner. The data verify that those strains can be cultivated on an industrial scale, and that the NTH1 and/or ATH1 gene disruption in those strains did not interfere with the requirements including the cell growability and the storage stability necessary to practical baker's yeast.

(Time-dependent Variation in Trehalose Content of Strain in Fed-batch Culture)

The cultivation process employed herein could be divided into two stages, one being a logarithmic growth phase stage and the other being a stationary phase stage.

Figure 11:
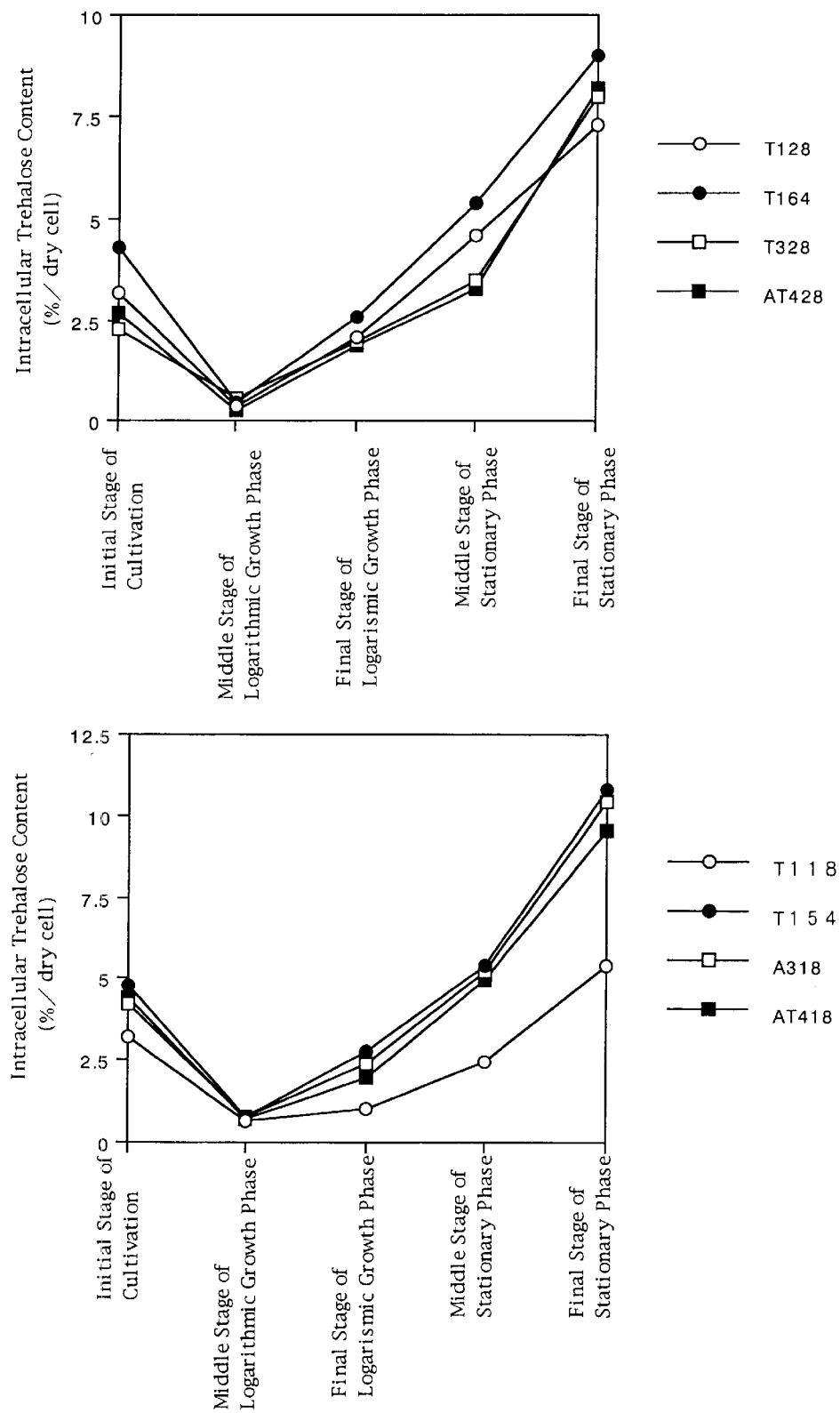
FIG. 11 shows the time-dependent variation in trehalose contents.

Of the strains in Tables 17, 18 and 19, cells of 8 strains of T118, T128, their NTH1 gene-disrupted strains, T154 and T164, their ATH1 gene-disrupted strains, A318 and A328, and their NTH1 and ATH1 genes-disrupted strains, AT418 and AT428, were cultivated under the condition noted above, while being sampled in the initial, middle and last stages in each phase, and their trehalose content was measured. The data obtained are shown in FIG. 11.

Strains T118 and T128 were named *Saccharomyces cerevisiae* T118 and *Saccharomyces cerevisiae* T128, respectively, and were deposited in the international depository authority, the National Institute of Bioscience and Human-Technology, Agency of Industrial Science and Technology of Japan, for FERM BP-6096 and FERM BP-6097, respectively. Their than gene-disrupted strains A318 and a328 were named *Saccharomyces cerevisiae* A318 and *Saccharomyces cerevisiae* A328, respectively, and were deposited in the same international depository authority for FERM BP-6039 and FERM BP-6040, respectively.

Comparing the wild strain T118 with its trehalase gene-disrupted strains T154 and A318, it is known that the gene disruption obviously resulted in the increase in the trehalose content of the gene-disrupted strains in the final stage of the cell culture, and the trehalose content of the gene-disrupted strains was about 2 times that of the wild strain. The NTH1 gene disruption and the ATH1 gene disruption gave nearly the same result. Comparing T154 and A318 with AT418 showed no synergistic effect of the disruption of the two genes, NTH1 and ATH1. This significantly differs from the above-mentioned report of John Kim, et al. (of the California University) who said that the trehalase gene disruption in baker's yeast resulted in the increase in the trehalose content of the yeast, that the effect of the ATH1 gene disruption is much larger than that of the NTH1 gene disruption, and that the ATH1 and NTH1 genes disruption gave a synergistic effect. It is believed that the difference between the data which John Kim, et al. obtained previously and those which we obtained herein will result from the difference between the laboratory strains which they tested and the practical strains which we tested and from the difference between the laboratory-scale batchwise culture which they tried in their test and the industrial-scale fed-batch culture which we tried in our test.

On the contrary, when the wild strain T128 is compared with its trehalase gene-disrupted strains, T164, A328 and AT428, it is known that the trehalose content of the gene-disrupted strains in the final stage of the cell culture was only slightly larger than that of the wild strain. Specifically, there was found no significant difference between the NTH1 gene disruption and the ATH1 gene disruption with respect to their effect on the trehalose accumulation in those strains and even no synergistic effect of the disruption of the two genes, NTH1 and ATH1.

In the test of practical baker's yeast strains for their capabilities, generally used are the cells having been cultivated in fed-batch culture as a simulation of industrial-scale culture, for example, in the manner mentioned above. In the test, the intracellular trehalose content could be 8+/−2% or so, relative to the dry cells, and the trehalose content of the wild strain T118 somewhat differs from that of practical baker's yeast strain generally used in the art. As so mentioned hereinabove, most laboratory yeast strains could not apply to the fed-batch culture system. If, however, they are intentionally cultivated in the fed-batch culture system test, while neglecting the production efficiency in the test, their trehalose content will fall between 2 and 4% or so, which significantly differs from the trehalose content of practical strains. In the test of other practical baker's yeast strains shown in the above-mentioned Tables, the ATH1 gene disruption in the wild strains, of which the trehalose content in the final stage of their culture is nearly the same as that of laboratory strains, like T118, resulted in significant increase in the amount of trehalose produced in the NTH1 or ATH1 gene-disrupted strains, but the effect of the NTH1 or ATH1 gene disruption in the other wild strains of which the trehalose production is nearly the same as that of practical baker's yeast generally used in the art was only small. In this point, the laboratory strains shall be differentiated from the practical baker's yeast strains.

EXAMPLE 6

NTH1 gene-disrupted strains, ATH1 gene-disrupted strains and NTH1 and ATH1 genes-disrupted strains were tested for their capabilities in bread production and for their activity in frozen dough.

(Bread Making Test of Wild Strains and Trehalase Gene-disrupted Strains)

Eight strains of T118, T128, their NTH1 gene-disrupted strains, T154 and T164, their ATH1 gene-disrupted strains A318 and A328, and their NTH1 and ATH1 genes-disrupted strains, AT418 and AT428, all cultivated in Example 5, and also a commercially-available baker's yeast (manufactured by Oriental Yeast Co., Ltd.) were used in preparing dough samples having the composition mentioned below. The samples were tested in accordance with the baker's yeast test method of the Japan Yeast Industry Association, under the bread making procedure shown in Table 20.

TABLE 20

|  | Low-sugar Dough (for loaves) | High-sugar Dough |
|---|---|---|
| (Formulation) | | |
| Wheat flour | 100 | 100 |
| Sugar | 5 | 30 |
| Salt | 2 | 0.5 |
| Yeast | 2 | 4 |
| Shortening | 5 | 6 |
| Skim milk | 0 | 2 |
| Water | 65 | 52 |
| Bread Making Procedure | | |
| Mixing | L2,M2,↓ L2,M2,H2~ | L3,M2,↓ L2,M2,H1~ |
| Mixing Temperature | 28° C. | 28° C. |
| First Fermentation | 30° C., 70 min | 30° C., 70 min |
| Second Fermentation | 30° C., 30 min | 30° C., 30 min |
| Dividing, Rounding | 450 g | 450 g |
| Bench | 30° C., 15 min | 30° C., 20 min |
| Shaping | One loaf | One loaf |
| Fermentation in Roaster | 38° C., RH 85%, 1.5 cm above loaf cup holder | 38° C., RH 85%, 1.5 cm above loaf cup holder |
| Bread Making | 200° C., 25 min | 200° C., 25 min |

The data obtained are shown in Table 21 and Table 22 below. There was found no significant difference between the wild strains and the trehalase gene-disrupted strains in the loaf dough bread making test.

TABLE 21

Loaf Dough Bread Making Test

| Strain Used | Volume of Loaf (ml) | Relative Volume of Loaf (ml/g) |
|---|---|---|
| T118 | 1,788 | 4.9 |
| T154 | 1,875 | 5.0 |
| T318 | 1,913 | 5.2 |
| AT418 | 1,825 | 4.9 |
| T128 | 1,938 | 5.2 |
| T164 | 1,950 | 5.2 |
| A328 | 1,962 | 5.3 |
| AT428 | 1,950 | 5.2 |
| Commercially-available Yeast | 1,855 | 5.1 |

TABLE 22

Bun Dough Bread Making Test

| Strain Used | Volume of Bun (ml) | Relative Volume of Bun (ml/g) |
|---|---|---|
| T118 | 1,788 | 4.3 |
| T154 | 1,950 | 4.7 |
| A318 | 1,950 | 4.7 |
| AT418 | 2,025 | 4.9 |
| T128 | 1,875 | 4.5 |
| T164 | 1,888 | 4.6 |
| A328 | 2,000 | 4.8 |
| AT428 | 1,850 | 4.4 |
| Commercially-available Yeast | 1,750 | 4.5 |

In the bun dough formulation tested herein, the trehalase gene-disrupted strains were significantly superior to the wild strains. Specifically, the ATH1 gene-disrupted strain A318 was more active than its wild strain T118; and the ATH1 gene-disrupted strain A328 was more active than its wild strain T128. The reason will be because the trehalase gene disruption resulted in the increase in the trehalose content of the gene-disrupted strains and in the trehalose content retentiveness thereof. Accordingly, the intracellular trehalose content of the gene-disrupted strains could be kept high, and the intracellular osmotic pressure in those strains could also be kept high. As a result, even in the high-sugar bun dough, the cells of the gene-disrupted strains could keep high fermentation power. The data of the gene-disrupted strains are well comparable to those of the commercially-available yeast.

(Frozen Dough Resistance Test)

Eight strains of T118, T128, their NTH1 gene-disrupted strains, T154 and T164, their ATH1 gene-disrupted strains A318 and A328, and their NTH1 and ATH1 genes-disrupted strains AT418 and AT428, all cultivated in Example 5, were used in preparing dough samples having the composition mentioned below. The samples were tested in accordance with the frozen dough bread making test method of the Japan Yeast Industry Association, under the bread making procedure mentioned below.

(Dough Formulation)

| Wheat flour | 100 g |
|---|---|
| Sugar | 5 g |
| Salt | 2 g |
| Yeast | 2 g |
| Shortening | 5 g |
| Water | 67 ml |

(Bread Making Procedure)

| Incubation before freezing | 60 minutes |
|---|---|
| Frozen period | 1 or 2 weeks (at −20° C.) |
| Thawing | 90 minutes (at 30° C.) |
| Rounding, Bench | 30 minutes |
| Shaping | |
| Fermentation in Roaster | 55 minutes |
| Baking | 25 minutes |

The data obtained are shown in Table 23 and Table 24 below. As compared with the wild strains, the trehalase gene-disrupted strains had significantly increased frozen dough resistance. The reason will be because the trehalase gene disruption resulted in the increase in the trehalose content of the gene-disrupted strains and also in the trehalose content retentiveness thereof. As a result, the gene-disrupted strains could have increased frozen dough resistance.

TABLE 23

Frozen Dough Bread Making Test 1

| Strain Used | Volume (1 week after freezing) | Specific Volume (1 week after freezing) |
|---|---|---|
| T118 | 505 | 3.4 |
| T154 | 590 | 4.1 |
| T318 | 555 | 3.7 |
| AT418 | 590 | 3.9 |

TABLE 24

Frozen Dough Bread Making Test 2

| | 1 week after freezing | | 2 weeks after freezing | |
| --- | --- | --- | --- | --- |
| | Volume | Specific Volume | Volume | Specific Volume |
| T128 | 730 | 4.8 | 615 | 4.0 |
| T164 | 740 | 4.9 | 655 | 4.3 |
| A328 | 740 | 4.9 | 635 | 4.2 |
| AT428 | 740 | 4.9 | 650 | 4.3 |

In all tests, it is known that the baking capabilities of the gene-disrupted strains are comparable to or higher than those of the commercially-available baker's yeast strain. Obviously, in addition, the trehalase gene-disrupted strains have higher frozen dough resistance than the wild strain.

EXAMPLE 7

NTH1 gene-disrupted strains, ATH1 gene-disrupted strains and NTH1 and ATH1 genes-disrupted strains were tested for their drying resistance, in the manner mentioned below.

Precisely, cells of the strains having been obtained in Example 5 were dewatered to have a water content of at most 68%. Thus was prepared 1.5 kg of pressed raw yeast from each strain. To this was added an aqueous emulsion of sorbitan fatty acid ester in an amount of from 1.5 to 2.0% relative to the dried yeast, and mixed. The resulting mixture was passed through a 0.4 no screen mesh in an extruder. The resulting strings were dried in a fluidized bed drier, in which the temperature of hot air was 50° C. at the inlet, about 10 minutes. After that and just before the temperature of the pellets being dried increased, the inlet temperature was lowered to be 38° C. The pellets were further dried about 50 minutes. In that stage, the temperature of the pellets being dried was not higher than 38° C. The drying end point was when the water content of the dried pellets was 5+/−0.3% as measured with an infrared water content meter. The dried samples were separately stored in vacuum packages.

Figure 12:
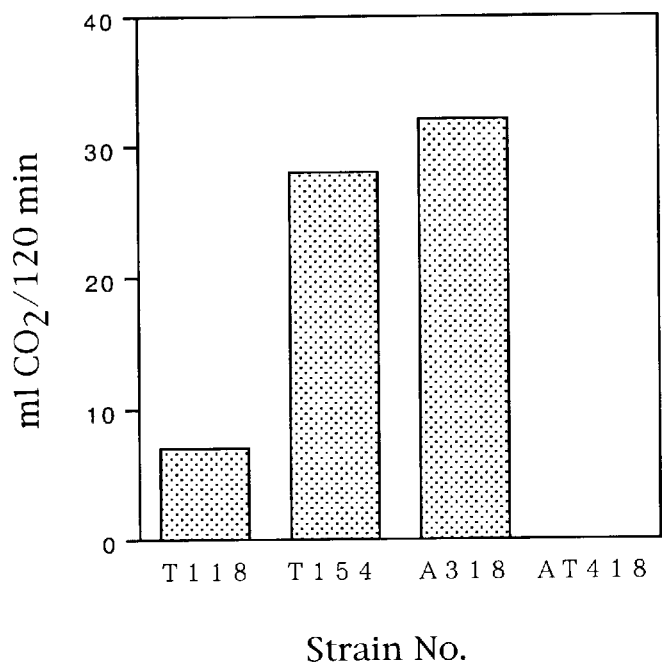
FIG. 12 shows the data of drying resistance test 1.
Figure 13:
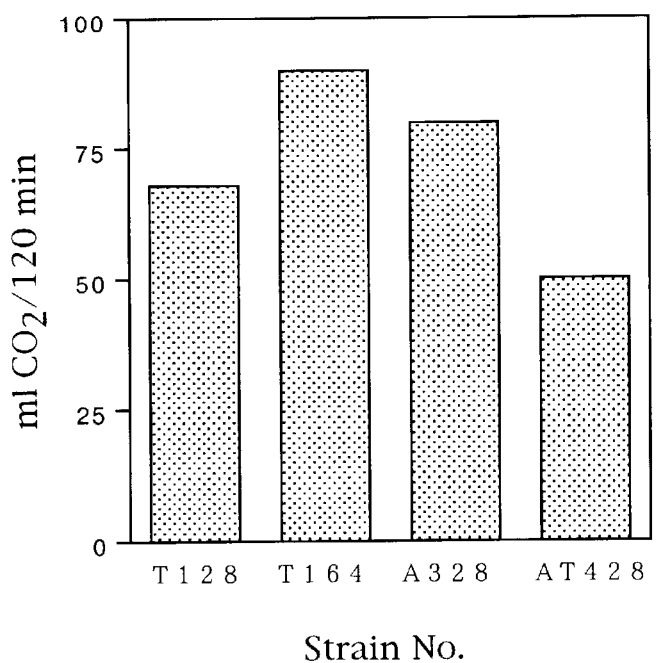
FIG. 13 shows the data of drying resistance test 2.

Each dry yeast sample was suspended in water at 40° C. to have a concentration of 3.1%. 5 ml of each yeast suspension was mixed with 15 ml of 13.33% sucrose solution to give 20 ml of a $CO_2$ production test liquid. Each test liquid was tested for its $CO_2$ production capacity within a period of 120 minutes, according to the baker's yeast test method of the Japan Yeast Industry Association. The data obtained are shown in FIG. 12 and FIG. 13.

The ATH1 or NTH1 gene-disrupted strains got good drying resistance. As opposed to those, it is obvious that the drying resistance of the ATH1 and NTH1 genes-disrupted strains is comparable to or lower than that of the wild strains. As in FIG. 12 and FIG. 13, the gene-disrupted strains all have a higher trehalose content than the wild strains. This indicates that the mere increase in their trehalose content could not get the cells drying resistance necessary to baker's dry yeast. Trehalose in baker's yeast cells has some influences on the drying resistance, the freezing resistance and the osmotic pressure resistance of the cells. In addition, it has an additional influence on the storability (the shelf-life) of practical baker's yeast. Specifically, the trehalose content of practical baker's yeast gradually decreases while the yeast is stored. During its storage, practical baker's yeast consumes trehalose as the energy source for retaining its activity, and the yeast s trehalose consumption corresponds to the decrease in the trehalose content of the yeast. Dry baker's yeast requires trehalose which acts as the protecting agent while yeast is dried, and consumes trehalose as the energy source when the dry yeast is re-hydrated with water. Therefore, dry baker's yeast not having a satisfactory degree of trehalase activity when it is re-hydrated with water could not ensure the energy necessary to its re-activation. Even if the survival rate of yeast cells being dried and re-hydrated is high, such does not directly meet the requirement for dry baker's yeast.

Yeast strains Saccharomyces cerevisiae of the same species may have different degrees of intracellular enzymatic activity. As is obvious from the comparison between the data of practical baker's yeast strains shown in the report of Takano, et al. (of National Food Research Institute of the Ministry of Agriculture, Forestry and Fisheries of Japan, red in the Meeting of the Japanese Society for Food Science and Technology in 1997) and in their patent application, Japanese Patent Application No. 9-352016 for ATH1 gene disruption, and those of laboratory strains shown in the report of Monika Destruelle, et al. (of the Freiburg University and in the report of Helmut Holzer, et al. (of the Freiburg University) (see J.B.C. Vol. 268, No. 7, 1993), the trehalase activity of practical baker's yeast strains is higher than that of laboratory strains. Through disruption of either one of trehalase genes in practical strains, the gene-disrupted practical strains got a suitable degree of trehalase activity, or that is they were so modified through the gene disruption that they could have a suitable trehalose content necessary for their drying resistance and could consume trehalose as the energy source when they are re-hydrated with water to exhibit their dough-expanding activity. However, it cannot be considered that laboratory strains could get the same results.

Figure 14:
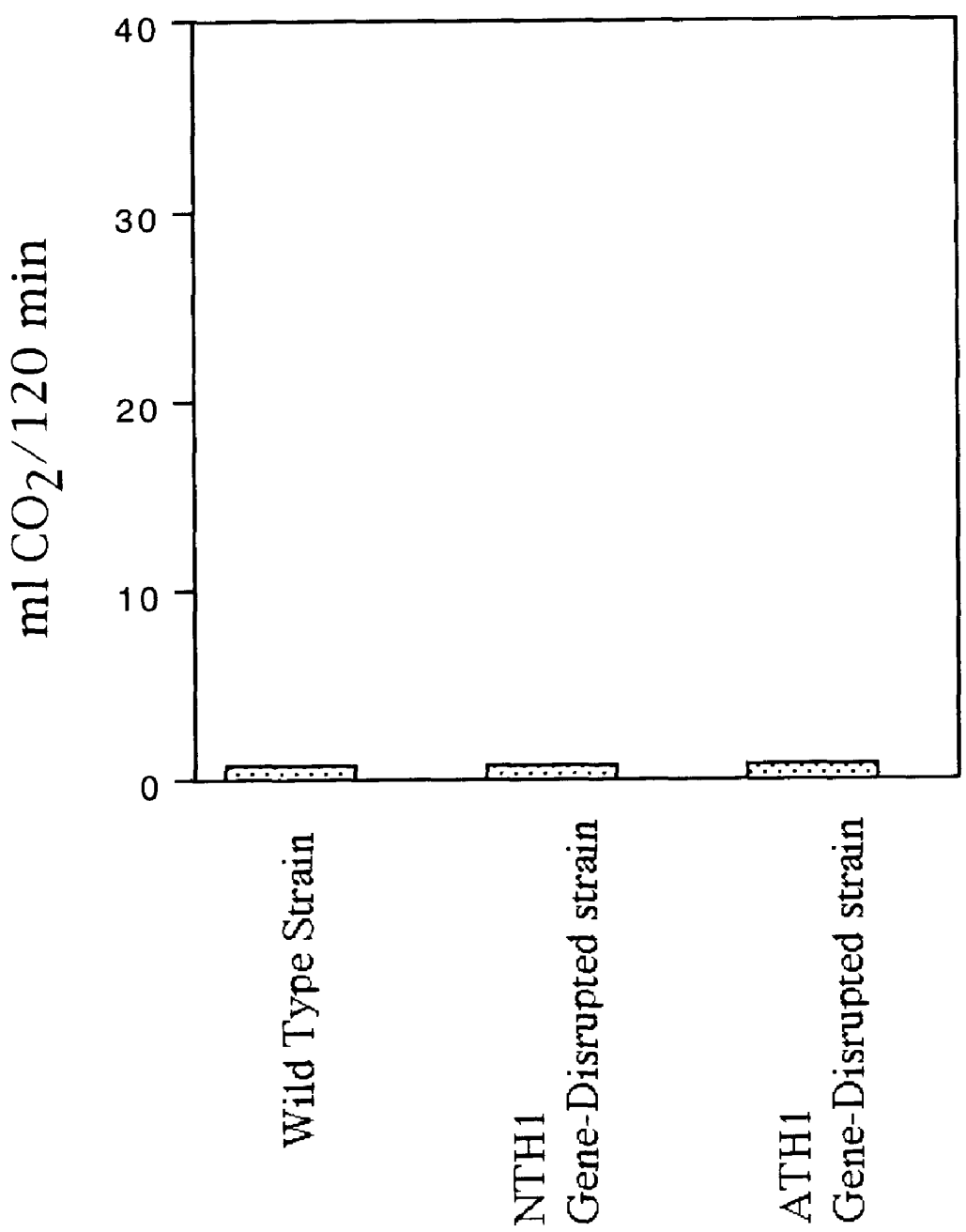
FIG. 14 shows the data of drying resistance test 3.

Standard laboratory strains of yeast Saccharomyces cerevisiae, X2180–1A (a-type) and X2180–1B (α-type) (these are known, for example, in a catalogue from the Yeast Genetic Stock Center of the California University) were processed in the same manner as above to prepare an NTH1 gene-disrupted diploid strain and an ATH1 gene-disrupted diploid strain, and these strains were subjected to the drying resistance test. The test data are shown in FIG. 14 (Drying Resistance Test-3).

From the data as above, it is known that the baking capabilities of the ATH1 gene-disrupted strains, the NTH1 gene-disrupted strains and the ATH1 and NTH1 genes-disrupted strains are comparable to those of the non-disrupted strains, and the gene-disrupted strains are usable as practical baker's yeast. In addition, the frozen dough resistance of all those gene-disrupted strains is higher than that of the wild strains. The high-sugar dough resistance of the ATH1 gene-disrupted strains and the ATH1 and NTH1 genes-disrupted strains has increased. Regarding the drying resistance of those strains, however, the drying resistance of the ATH1 gene-disrupted strains and the NTH1 gene-disrupted strains has increased, but the drying resistance of the ATH1 and NTH1 genes-disrupted strains is the same as or lower than that of the wild strains. We, the present inventors have clarified this fact for the first time, and the fact could not be easily derived from the reasoning previously made by some persons who used laboratory strains

EFFECTS OF THE INVENTION

The ATH1 and/or NTH1 gene-disrupted strains of the invention are of extremely excellent, drying-resistant practical baker's yeast, and the baker's yeast of the invention can be in the form of dry yeast not requiring sugared water for its re-activation but capable of being easily re-activated only with water within a short period of time. Therefore, the dry baker's yeast of the invention can be directly mixed with dough and it can be immediately re-activated in dough. In addition, the baker's yeast of the invention is widely applicable in producing any type of bread.

SEQUENCE LISTING

Sequence Numbers 1 and 2 indicate primer 1 and primer 2, respectively, for PCR. Sequence Number 3 indicates the amino acid-coding region of ATH1 gene. Sequence Number 4 indicates the full-length region of URA3 gene.

Tables 1 to 14 below show the sequences of Sequence Numbers 1 to 4.

What is claimed is:

1. A method for producing a dry diploid baker's yeast of *Saccharomyces cerevisiae* comprising:
   a. producing a/α-type diploid yeasts by mating an a-type haploid yeast with an α-type haploid yeast to produce an a/α-diploid yeast;
   b. selecting an a/α-type diploid yeast from the a/α-type diploid yeasts produced in step (a) by cultivating each yeast and by making bread using each yeast, and selecting the yeasts with the following characteristics:
      (i) primary points
         ability to grow in a blackstrap molasses medium;
         separability of the cultivated yeast from the medium;
         dehydration efficiency in forming the product of yeast;
         ability to maintain dough-expanding activity during long-term cold storage;
         resistance to softening of the yeast during long-term cold storage;
         ability of the yeast to maintain its color without absorbing the color of blackstrap molasses; and
      (ii) secondary point taste of bread produced with the yeast;
   c. disrupting the ATH1 genes of the same a-type and α-type haploid yeasts used to produce the diploid yeast selected in step (b) by inserting a marker'selected from the group consisting of URA3, LYS2 and ADE2 into the respective ATH1 genes, wherein the respective NTH1 genes of the same a-type and α-type haploid yeasts used to produce the diploid yeast selected in step (b) are not disrupted;
   d. mating the ATH1 gene-disrupted a-type haploid yeast obtained in step (c) with the ATH1 gene-disrupted alpha-type haploid yeast obtained in step (c) to produce an ATH1 gene-disrupted diploid yeast;
   e. culturing the ATH1 gene-disrupted a/α-type diploid yeast obtained in step (d);
   f. recovering the cultured yeast;
   g. pressing the recovered yeast; and
   h. drying the pressed yeast by fluidized bed drying.

2. A method for producing a dry diploid baker's yeast of *Saccharomyces cerevisiae* comprising:
   a. producing a/α-type diploid yeasts by mating an a-type haploid yeast with an α-type haploid yeast to produce an a/α-diploid yeast;
   b. selecting an a/α-type diploid yeast from the a/α-type diploid yeasts produced in step (a) by cultivating each yeast and by making bread using each yeast, and selecting the yeasts with the following characteristics:
      (i) primary points
         ability to grow in a blackstrap molasses medium;
         separability of the cultivated yeast from the medium;
         dehydration efficiency in forming the product of yeast;
         ability to maintain dough-expanding activity during long-term cold storage;
         resistance to softening of the yeast during long-term cold storage;
         ability of the yeast to maintain its color without absorbing the color of blackstrap molasses; and
      (ii) secondary point taste of bread produced with the yeast;
   c. disrupting the NTH1 genes of the same a-type and α-type haploid yeasts used to produce the diploid yeast selected in step (b) by inserting a marker'selected from the group consisting of URA3, LYS2 and ADE2 into the respective NTH1 genes, wherein the respective ATH1 genes of the same a-type and α-type haploid yeasts used to produce the diploid yeast selected in step (b) are not disrupted;
   d. mating the NTH1 gene-disrupted a-type haploid yeast obtained in step (c) with the NTH1 gene-disrupted α-type haploid yeast obtained in step (c) to produce an NTH1 gene-disrupted diploid yeast;
   e. culturing the NTH1 gene-disrupted a/α-type diploid yeast obtained in step (d);
   f. recovering the cultured yeast;
   g. pressing the recovered yeast; and
   h. drying the pressed yeast by fluidized bed drying.

3. A biologically pure culture of *Saccharomyces cerevisiae* A318, FERM BP-6039.

4. A biologically pure culture of *Saccharomyces cerevisiae* A328, FERM BP-5678.

5. Dry diploid baker's yeast made by the method according to claim 2.

6. Dry diploid baker's yeast made by the method according to claim 1.

* * * * *